(12) United States Patent
Fernandez et al.

(10) Patent No.: US 9,073,856 B2
(45) Date of Patent: Jul. 7, 2015

(54) PHENYL METHANESULFONAMIDE DERIVATIVES USEFUL AS MGAT-2 INHIBITORS

(71) Applicant: Eli Lilly and Company, Indianapolis, IN (US)

(72) Inventors: Maria Carmen Fernandez, Madrid (ES); Maria Rosario Gonzalez-Garcia, Madrid (ES); Bin Liu, Fishers, IN (US); Lance Allen Pfeifer, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 14/372,606

(22) PCT Filed: Jan. 16, 2013

(86) PCT No.: PCT/US2013/021617
§ 371 (c)(1),
(2) Date: Jul. 16, 2014

(87) PCT Pub. No.: WO2013/112323
PCT Pub. Date: Aug. 1, 2013

(65) Prior Publication Data
US 2014/0371269 A1    Dec. 18, 2014

Related U.S. Application Data

(60) Provisional application No. 61/617,090, filed on Mar. 29, 2012.

(30) Foreign Application Priority Data

Jan. 23, 2012   (EP) ..................... 12382018

(51) Int. Cl.
| | |
|---|---|
| C07D 211/18 | (2006.01) |
| A61K 31/445 | (2006.01) |
| C07D 211/14 | (2006.01) |
| C07D 401/04 | (2006.01) |
| C07D 417/04 | (2006.01) |
| C07D 277/64 | (2006.01) |
| C07D 295/03 | (2006.01) |
| C07D 211/42 | (2006.01) |
| C07D 211/44 | (2006.01) |
| C07D 213/06 | (2006.01) |
| C07D 213/24 | (2006.01) |
| C07D 211/46 | (2006.01) |

(52) U.S. Cl.
CPC ............ *C07D 211/14* (2013.01); *C07D 401/04* (2013.01); *C07D 417/04* (2013.01); *C07D 277/64* (2013.01); *C07D 295/03* (2013.01); *C07D 211/42* (2013.01); *C07D 211/44* (2013.01); *C07D 213/06* (2013.01); *C07D 213/24* (2013.01); *C07D 211/18* (2013.01); *C07D 211/46* (2013.01)

(58) Field of Classification Search
CPC .. C07D 211/14; C07D 211/18; C07D 211/42; C07D 211/46; C07D 401/04; C07D 417/04
USPC .......... 546/194, 198, 209, 216, 232; 514/318, 514/321, 326, 327, 331
See application file for complete search history.

(56) References Cited

U.S. PATENT DOCUMENTS

| | | | |
|---|---|---|---|
| 5,889,006 A | 3/1999 | Lowe et al. | |
| 6,248,756 B1 * | 6/2001 | Anthony et al. | ............... 514/326 |
| 6,303,816 B1 | 10/2001 | Arnold et al. | |
| 6,387,954 B1 | 5/2002 | Jones et al. | |
| 6,500,865 B1 | 12/2002 | Arnold et al. | |
| 7,868,005 B2 * | 1/2011 | Rosenblum et al. | ...... 514/252.11 |
| 8,575,352 B2 | 11/2013 | Fernandez et al. | |
| 2009/0163545 A1 | 6/2009 | Goldfarb | |
| 2009/0221577 A1 | 9/2009 | Branch et al. | |
| 2010/0093771 A1 | 4/2010 | Nakamura et al. | |
| 2011/0015198 A1 | 1/2011 | Kamijo et al. | |
| 2011/0275647 A1 | 11/2011 | Arakawa et al. | |

FOREIGN PATENT DOCUMENTS

| | | |
|---|---|---|
| EP | 1655283 | 8/2004 |
| EP | 1659113 | 8/2004 |
| EP | 2078719 | 9/2014 |
| WO | WO9738665 | * 10/1997 |

(Continued)

OTHER PUBLICATIONS

Anthony et al. "Preparation of . . . " CA127:3588860 (1997).*
Chemcats, RN 1455245-94-9 (2015).*
Rosenblum et al. "Pyrazinyl-substituted . . . " CA145:271804 (2006).*
Yen, et al., "MGAT2, a Monoacylglycerol Acyltransferase Expressed in the Small Intestine," The Journal of Biological Chemistry, vol. 278, No. 20, Issue of May 16, pp. 18532-18537 (2003).

(Continued)

*Primary Examiner* — Celia Chang
(74) *Attorney, Agent, or Firm* — James B. Myers

(57) ABSTRACT

The present invention provides compounds of Formula I or a pharmaceutical salt thereof, where the variables for R1, R2, and R3 are as described herein; methods of treating a condition such as hypertriglyceridemia; and processes for preparing the compounds.

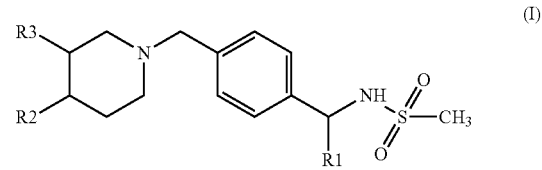

(I)

15 Claims, No Drawings

(56) References Cited

FOREIGN PATENT DOCUMENTS

| WO | 2010095767 | 8/2010 |
|---|---|---|
| WO | 2012091010 | 5/2012 |
| WO | 2013112323 | 8/2013 |
| WO | 2013116065 | 8/2013 |
| WO | 2014074365 | 5/2014 |

OTHER PUBLICATIONS

Hall, et al., "Evidence for regulated monoacylglycerol acyltransferase expression and activity in human liver," Journal of Lipid Research, vol. 53, pp. 990-999 (2012).

Cao, et al., "A Predominant Role of Acyl-CoA:monoacylglycerol Acyltransferase-2 in Dietary Fat Absorption Implicated by Tissue Distribution, Subcellular Localization, and Up-regulation by High Fat Diet," The Journal of Biological Chemistry, vol. 279, No. 18, Issue of Apr. 30, pp. 18878-18886 (2004).

Yen, et al., "Deficiency of the intestinal enzyme acyl CoA:monoacylglycerol acyltransferase-2 protects mice from metabolic disorders induced by high-fat feeding," Nature Medicine, vol. 15, No. 4, pp. 442-446 (2009).

Olsson, et al, "Rosuvastatin: A Highly Effective New HMG-CoA Reductase Inhibitor," Cardiovascular Drug Reviews, vol. 20, No. 4, pp. 303-328, (2002).

* cited by examiner

PHENYL METHANESULFONAMIDE DERIVATIVES USEFUL AS MGAT-2 INHIBITORS

Triacylglycerol, (or triglyceride) accounts for more than 90% of the dietary fat for humans. This is thought to be because of the nearly complete absorption of triacylglycerol in the small intestine. This may have a profound effect on a person's health because an excess of dietary fat is a leading cause of diet induced obesity.

The enzyme acyl CoA:monoacylglycerol acytransferase-2 (MGAT-2) is believed to play an important role in the absorption of dietary fat in the small intestines. It has been demonstrated that MGAT-2 deficient mice when fed a high fat diet, are protected against developing obesity, glucose intolerance, hypercholesterolemia and developing a fatty liver. Further, it has been shown that MGAT-2 deficient mice exhibit lower plasma triacylglycerol levels after a dietary oil challenge. (Yen, et al, *Nat. Med.* 2009, 15(4), 442-446.)

There is a need for alternative drugs and treatment for hypertriglyceridemia. The present invention addresses this need by providing alternative compounds and treatment methods, which may be suitable for the treatment hypertriglyceridemia.

The present invention provides a compound of Formula I:

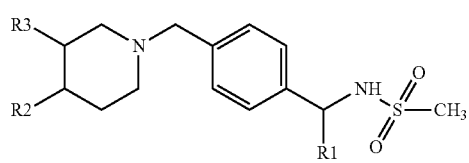

wherein R1 is selected from: —CH$_3$ and —CF$_3$; R2 is selected from H, —C$_{1-4}$alkyl, —C$_{3-4}$cycloalkyl, —C$_{1-2}$alkylcyclopropyl, —O—C$_{1-2}$alkyl, phenyl, 2-benzothiazolyl, 2-pyridinyl, and 3-pyridinyl, wherein the phenyl is optionally substituted with 1 or 2 groups independently selected from: halo, —C$_{1-2}$alkyl, —CF$_3$, —OC$_{1-3}$alkyl, and —OC$_{1-2}$haloalkyl, and the pyridinyl is optionally substituted with 1 or 2 groups independently selected from —CH$_3$, halogen, —OCH$_2$cyclopropyl, and —OC$_{1-3}$alkyl; and R3 is selected from: H, —C$_{1-4}$alkyl, —OC$_{1-3}$alkyl, —OC$_{1-2}$haloalkyl, phenyl, 2-pyridinyl, 3-pyridinyl, 4-pyridinyl, and 2-thiazolyl, wherein the phenyl is optionally substituted with a halogen atom; and provided that if one of R2 and R3 is H then the other one of R2 and R3 is not H; or a pharmaceutically acceptable salt thereof.

The present invention provides compounds as described above for Formula I, or a pharmaceutically acceptable salt thereof wherein in one embodiment, R1 is —CH$_3$.

The present invention provides compounds as described above for Formula I, or a pharmaceutically acceptable salt thereof wherein in another embodiment R1 is —CF$_3$.

The present invention provides compounds as described above for Formula I, or a pharmaceutically acceptable salt thereof wherein preferably R2 is selected from: —C$_{1-4}$alkyl, —C$_{3-4}$cycloalkyl, —O—CH$_3$, and phenyl, wherein the phenyl is optionally substituted with a halogen. More preferably R2 is selected from: —C(CH$_3$)$_3$, cyclopropyl, —O—CH$_3$, and phenyl, wherein the phenyl is optionally substituted with halogen. Still more preferably, R2 is selected from —C(CH$_3$)$_3$, —O—CH$_3$ and 4-fluorophenyl.

The present invention provides compounds as described above for Formula I, or a pharmaceutically acceptable salt thereof wherein preferably R3 is selected from: H, phenyl, —O—CH$_3$, 2-pyridinyl, 3-pyridinyl, and 2-thiazolyl, wherein the phenyl is optionally substituted with a halogen atom. More preferably R3 is selected from: H, phenyl, and 2-thiazolyl, wherein the phenyl is optionally substituted with a halogen atom. In one preferred form, R3 is H.

The present invention provides compounds of Formula I, or pharmaceutically acceptable salts thereof, wherein R1 is —CH$_3$ or —CF$_3$; R2 is selected from: —C$_{1-4}$alkyl, —C$_{3-4}$cycloalkyl, —O—CH$_3$, and phenyl, wherein the phenyl is optionally substituted with a halogen; and R3 is selected from: H, phenyl, —OCH$_3$, 2-pyridinyl, 3-pyridinyl, and 2-thiazolyl, wherein the phenyl is optionally substituted with a halogen.

The present invention provides compounds of Formula I, or pharmaceutically acceptable salts thereof, wherein R1 is —CH$_3$ or —CF$_3$; R2 is selected from —C$_{1-4}$alkyl, —C$_{3-4}$cycloalkyl, —O—CH$_3$, and phenyl, wherein the phenyl is optionally substituted with a halogen; and R3 is selected from: H, phenyl, and 2-thiazolyl, wherein the phenyl is optionally substituted with a halogen.

The present invention provides compounds of Formula I, or pharmaceutically acceptable salts thereof, wherein R1 is —CH$_3$ or —CF$_3$; R2 is selected from —C(CH$_3$)$_3$, cyclopropyl, —OCH$_3$, and phenyl, wherein the phenyl is optionally substituted with a halogen; and R3 is selected from: H, phenyl, —OCH$_3$, 2-pyridinyl, 3-pyridinyl, wherein the phenyl is optionally substituted with a halogen atom.

The present invention provides compounds of Formula I, or pharmaceutically acceptable salts thereof, where R1 is —CH$_3$ or —CF$_3$; R2 is selected from —C$_{1-4}$alkyl, —C$_{3-4}$cycloalkyl, —C$_{1-2}$alkylcyclopropyl, phenyl, 2-benzothiazolyl, 2-pyridinyl and, 3-pyridinyl, wherein the phenyl is optionally substituted with 1 or 2 groups independently selected from: halo, —C$_{1-2}$alkyl, —CF$_3$, —OC$_{1-3}$alkyl, and —OC$_{1-2}$haloalkyl, and the pyridinyl is optionally substituted with 1 or 2 groups independently selected from —CH$_3$, halo, —OCH$_2$cyclopropyl, and —OC$_{1-3}$alkyl; and R3 is H. More preferably R2 is selected from —C$_{1-4}$alkyl, —C$_{3-4}$cycloalkyl, and phenyl, wherein the phenyl is optionally substituted with a halogen substituent and R3 is H; still more preferably R2 is selected from: —C(CH$_3$)$_3$, cyclopropyl, phenyl, wherein the phenyl is optionally substituted with a halogen substituent and R3 is H; still more preferably, R2 is —C(CH$_3$)$_3$ or 4-fluorophenyl and R3 is H.

The present invention provides compounds of Formula I, or a pharmaceutically acceptable salt thereof, wherein R1 is —CF$_3$; R2 is —C(CH$_3$)$_3$ or —OCH$_3$; and R3 is selected from: H or 2-thiazolyl.

A particularly preferred compound of the present invention is N-[(1S)-1-[4-[(4-tert-butyl-1-piperidyl)methyl]phenyl]-2,2,2-trifluoro-ethyl]methanesulfonamide, or a pharmaceutically acceptable salt thereof. Preferably the counterion of the pharmaceutically acceptable salt is chloride or phosphate.

Preferred compounds of the present invention have the formula illustrated below for Figure Ia where one of the stereocenters has the configuration illustrated below with a single asterisk, *.

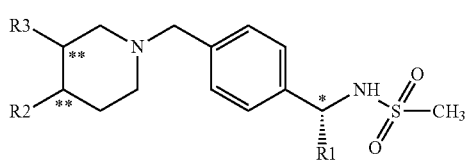

where R1, R2 and R3 are as described above. Depending upon the specific R2 and R3 groups selected, molecules of the present invention can also include additional stereocenters illustrated above with a double asterisk, **.

The present invention provides a pharmaceutical composition comprising a compound according to Formula I or Ia or a pharmaceutically acceptable salt thereof and at least one of a pharmaceutically acceptable carrier, diluent, or excipient. Preferably the pharmaceutical composition comprises a compound according to Formula Ia in greater than 85% ee, still more preferably in greater than 90% ee, and still more preferably in greater than 95% ee.

The present invention provides a method of treating hypertriglyceridemia in a patient in need of treatment thereof. The method comprises administering to the patient in need, an effective amount of a compound according to Formula I or Ia, or a pharmaceutically acceptable salt thereof.

The present invention also provides a compound of formula I or Ia, or a pharmaceutically acceptable salt thereof, for use in therapy. In one form, the use of the compound, or a pharmaceutically acceptable salt thereof, is useful for the treatment of hypertriglyceridemia.

The present invention also provides for the use of a compound of formula I or Ia, or a pharmaceutically acceptable salt thereof, in the manufacture of a medicament for the treatment of hypertriglyceridemia.

The term "pharmaceutically-acceptable salt" refers a salt of the compound of the invention considered to be acceptable for clinical and/or veterinary use. Pharmaceutically acceptable salts and common methodology for preparing them are well known in the art. See, e.g., P. Stahl, et al., Handbook of Pharmaceutical Salts: Properties, Selection and Use, (VCHA/Wiley-VCH, 2002); S. M. Berge, et al., "Pharmaceutical Salts," *Journal of Pharmaceutical Sciences*, Vol. 66, No. 1, January 1977.

The present invention provides pharmaceutically acceptable salts of the compounds of Formula I as described above. Preferred salts of the present invention include salts where the counter ion is/are phosphate or one or more chloride(s).

The term alkyl as used herein is a straight chained alkyl such as ethyl or n-propyl, or a branched chain alkyl such as isopropyl or tert-butyl. Preferably, the alkyl is a branched alkyl chain more preferably an isopropyl alkyl group or a tert-butyl group. The term cycloalkyl as used herein refers to cyclic hydrocarbons such cyclopropyl and cyclobutyl groups. The term alkylcyclopropyl as used herein refers to a substituent in which the alkyl portion is attached to the rest of the molecule. The alkyl group attached to the cyclopropyl can be a straight chain or branched chain. The alkyl group is also attached to the cyclopropyl group, either at a terminal, secondary carbon as in —CH$_2$CH(cyclopropyl)CH$_3$, or a tertiary carbon as in —CH$_2$—CH$_2$—CH$_2$-cycloalkyl. The term C$_{1-2}$ haloalkyl refers to a hydrocarbon group having one or two carbon atoms that has 1, 2, 3, or more halogen groups attached to the carbons of the alkyl chain. If there are two or more halogens, the halogens may but need not be attached to the same carbon. This term also includes perhalo alkyls where all the hydrogen atoms of the alkyl group are replaced with a halogen, for example, —CF$_3$.

As used herein patient refers to a mammal, preferably a human.

As used herein, the following terms have the meanings indicated: "ACN" refers to acetonitrile; "Boc" means tert-butyloxycarbonyl; "DCM" refers to dichloromethane; "de" refers to diastereomeric excess; "DMEA" refers to dimethylethanolamine; "ee" refers to enantiomeric excess; "EtOAc" refers to ethylacetate; "EtOH" refers to ethanol; "IPA" refers to isopropyl alcohol; "LC/MS" refers to liquid chromatography followed by mass spectroscopy; "MeOH" refers to methanol; "MS" refers to mass spectroscopy; "NMR" refers to nuclear magnetic resonance; "RP-C18" refers to C18 reverse phase column; "t-Bu" means a tertiary-butyl radical; "THF" refers to tetrahydrofuran; 'SFC" refers to supercritical fluid chromatography.

Unless noted to the contrary, the compounds illustrated herein are named and numbered using either ACDLABS or Symyx Draw 3.2.

General Chemistry

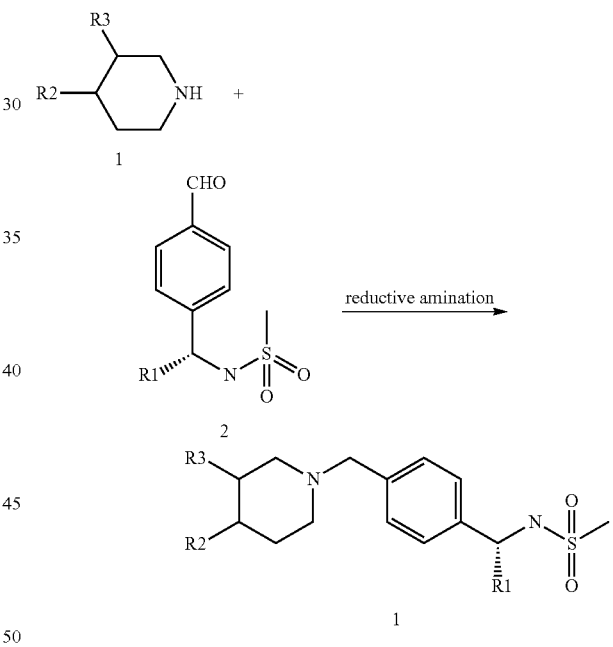

Scheme 1

Scheme 1 illustrates the general synthesis of compound of Formula I.

A substituted piperidine compound 1, which is either commercially available or synthesized by well known literature methods, is reacted with the compound 2 under reductive amination conditions well known to skilled artisans to provide the compound of Formula I. The substituted piperidine can be a mono substituted piperidine where one of R2 or R3 is hydrogen or di-substituted piperidine where neither R2 or R3 is a hydrogen. ((See: Richard C. Larock, *Comprehensive Organic Transformations: a guide to functional group preparations*, 2$^{nd}$ edition, Page 835-846, Wiley-VCH, (1999)). More specifically, compound 1 reacts with compound 2 with the existence of a proper reducing agent such as triacetoxyborohydride and a suitable acid such as acetic acid in a proper solvent such as dichloromethane to provide the compound of Formula I. which can be converted to a suitable salt with proper acids such as HCl and H₃PO₄.

Preparation 1

(N—Z)—N-[(4-Bromophenyl)methylene]-(R)-2-methyl-propane-2-sulfinamide

Add (R)-2-methylpropane-2-sulfinamide (40.5 g, 0.33 mol) portionwise to a solution of 4-bromobenzaldehyde (65.57 g, 0.35 mol) in toluene (283 mL). Stir the mixture at ambient temperature for 15 minutes, and then add sodium hydroxide (1.34 g, 0.33 mol). Stir the suspension at ambient temperature for 12 hours. Add sodium sulphate (16 g) and Celite® (16 g), and stir the suspension for 15 minutes. Then filter and concentrate the filtrate under vacuum. Purify the residue by silica gel chromatography eluting with hexane/ethyl acetate (100% to 70% hexane) to afford the title compound as a white solid (85.5 g, 88% yield). MS (m/z): 288 (M+1).

Preparation 2

N-[(1S)-1-(4-Bromophenyl)-2,2,2-trifluoro-ethyl]-(R)-2-methyl-propane-2-sulfinamide Add neat (trifluoromethyl)trimethylsilane (109 mL, 0.74 mol) at 0° C. to a stirred solution of tetrabutylammonium acetate (88 g, 0.29 mol) and (N—Z)—N-[(4-bromophenyl)methyl]-(R)-2-methyl-propane-2-sulfinamide (85 g, 0.29 mol) in dimethylformamide (1.2 L) at 0° C. Stir the mixture at 0-5° C. for 90 minutes. Add saturated aqueous ammonium chloride solution (1.2 L) and extract with EtOAc (4×400 mL). Combine and sequentially wash the organic phase with water then brine (2×1 L); dry over magnesium sulphate; filter; and concentrate the filtrate under vacuum. Triturate the residue with hexane (200 mL) for 10 minutes, filter and dry the filtrate under vacuum to afford the title compound as a yellow solid (81 g, 76% yield, >98 de). MS (m/z): 358 (M+1).

Preparation 3

(1S)-1-(4-Bromophenyl)-2,2,2-trifluoroethanamine

Add HCl (4M in dioxane, 226 mL, 0.9 mol) to a suspension of N-[(1S)-1-(4-bromophenyl)-2,2,2-trifluoro-ethyl]-(R)-2-methyl-propane-2-sulfinamide (81 g, 0.23 mol) in MeOH (670 mL). Stir at ambient temperature for one hour. Remove the solvent under vacuum and triturate the residue with methyl tert-butyl ether (200 mL) for 10 minutes to give the HCl salt as a brown solid. Dissolve the salt in water (1.2) and add 2N NaOH solution up to pH 10. Extract the mixture with methyl tert-butyl ether (3×500 mL). Wash the organic phase with water then brine (500 mL each); dry over magnesium sulphate; filter; and concentrate the filtrate under vacuum to give the title compound as a yellow solid (46 g, 80% yield, 98% ee). MS (m/z): 358 (M+1).

Preparation 4

N-[(1S)-1-(4-Bromophenyl)-2,2,2-trifluoro-ethyl]methanesulfonamide

Add methanesulfonyl chloride (16.42 mL, 0.21 mol) dropwise to a mixture of (1S)-1-(4-bromophenyl)-2,2,2-trifluoroethanamine (49 g, 0.19 mol), 4-dimethylaminopyridine (1.18 g, 9.0 mmol), 2,6-lutidine (67 mL, 0.57 mol) in DCM (250 mL) at 0° C. Warm the mixture to ambient temperature and stir at that temperature for 20 hours. Dilute the reaction mixture with DCM (300 mL) and wash it sequentially with 2M HCl (2×200 mL), water (250 mL), then brine (250 mL). Collect the organic phase and dry over magnesium sulphate; filter; and concentrate under vacuum. Triturate the residue with hexane (200 mL) for 10 minutes, filter and dry the solid under vacuum to give the title compound as a pale brown solid (60 g, 93% yield, 98% ee). MS (m/z): 332 (M+1).

Preparation 5

N-[(1S)-2,2,2-Trifluoro-1-(4-formylphenyl)ethyl]methanesulfonamide

In a 2 L PARR reactor, add N-[(1S)-1-(4-bromophenyl)-2,2,2-trifluoro-ethyl]methanesulfonamide (30 g, 90 mmol), palladium(II) acetate (0.81 g, 3.6 mmol), butyldi-1-adamantylphosphine (3.89 g, 10.84 mmol) and tetramethylethylenediamine (10.50 g, 90 mmol) in toluene (1.5 mL). Seal the reactor and charge with Synthesis Gas (1:1 CO/H₂ at 75 psi). Stir the reaction mixture at 95° C. for 16 hours. Cool the mixture, vent and open the reactor. Filter the mixture through Celite® and concentrate the filtrate liquids under vacuum. Purify the crude residue by silica gel chromatography eluting with hexane/ethyl acetate (8:2 to 1:1) to afford the title compound (22.8 g, 90%, 80% ee). Enrich the chiral purity by using a chiral column: Chiralpak AS-H (2.1×25 cm, 5 uM) CO₂/EtOH (9:1) to get the title compound (19 g, 75% yield, 98% ee). MS (m/z): 282 (M+1).

Preparation 6

N-[(1R)-1-(4-Bromophenyl)ethyl]methanesulfonamide

To a mixture of (1R)-1-(4-bromophenyl)ethanamine (25 g, 0.12 mol) and triethylamine (51 mL, 0.36 mol) in DCM (250 mL) at 0° C., add methanesulfonyl chloride (13.44 mL, 0.17 mmol). Warm to ambient temperature and stir for 2.5 hours. Wash reaction mixture with 2M aqueous HCl (100 ml). Then sequentially wash organic phase with water then brine (2×100 mL). Dry the organic phase over anhydrous sodium sulphate; filter; and concentrate the filtrate under vacuum to give a residue. Triturate the residue with hexane (150 mL), filter and dry under vacuum to afford the title compound as a yellow solid (33.24 g, 96%, ee>98%). MS (m/z): 278 (M+1).

Preparation 7

N-[(1R)-1-(4-Formylphenyl)ethyl]methanesulfonamide

Mix N-[(1R)-1-(4-bromophenyl)ethyl]-methanesulfonamide (10 g, 35 mmol), (1,1'-bis(diphenylphosphino)-ferrocene)palladium(II) chloride (733 mg, 0.9 mmol), sodium carbonate (3.81 g, 35 mmol) and DMF (50 mL) in a 300 mL PARR reactor. Add triethylsilane (11.6 mL, 0.72 mmol) and purge the reactor with carbon monoxide three times. Then charge the reactor with carbon monoxide (50 psi) and stir the mixture at 90° C. for 15 hours. Cool the reactor to ambient temperature, filter over Celite® pad and wash with DCM (150 mL). Sequentially wash the filtrate with water then brine (2×80 mL). Concentrate the organic filtrate under vacuum to obtain the residue as an orange oil. Purify the crude by silica gel flash chromatography eluting with hexane/ethyl acetate (0 to 30% ethyl acetate) to provide the title compound (5.6 g, 70%, ee>98%). MS (m/z): 228 (M+1).

Preparation 8

4-tert-Butylpyridine hydrochloride

Add a solution of hydrogen chloride (4M in dioxane, 794.36 mmol, 198.59 mL) to 4-tert-butylpyridine (100 mL, 662 mmol) at 22° C. over 30 minutes. The internal temperature rises to 32° C.; control the exotherm with an ice-water bath and the by adjusting rate of the addition. Stir the mixture at 22° C. for one hour and concentrate. Wash the walls of the flask with EtOH. Dry the resulting solid under vacuum (1 mbar, 23-40° C.) to give the title compound as a white solid (119 g, 99%). MS (m/z): 136 (M-HCl+1).

Preparation 9

4-tert-Butylpiperidine hydrochloride

Place 4-tert-butylpyridine hydrochloride (50 g, 277 mmol) in a PARR reactor and add EtOH (350 mL) followed by platinum (IV) oxide (5.0 g, 22.02 mmol). Stir the mixture at 22° C. under a hydrogen atmosphere (500 psi) for 18 hours. Evacuate the excess hydrogen and filter the suspension the a Celite® pad. Concentrate the filtrate and dry the residue under vacuum (40° C., 5 mbar) to give the title compound as an off-white solid (45.1 g, 92%). 1H-NMR ($d_6$-DMSO) δ 0.83 (s, 9H), δ 1.2-1.5 (m, 3H), δ 1.7 (d, 2H), δ 2.7-2.8 (m, 2H), δ 3.2 (d, 2H), δ 8.7-9.3 (2 bs, 2H).

Preparation 10

1-Benzyl-4-isopropyl-pyridin-1-ium bromide

Add benzyl bromide (4.3 mL, 36.4 mmol) to a solution of 4-isopropylpyridine (4.8 mL, 36.4 mmol) in acetone (16.3 mL). Stir the reaction mixture at 55° C. overnight. Concentrate the solvent and add diethyl ether. Sonicate the mixture and then decant the solvent. Dry the solid under vacuum to obtain the title compound as a pale yellow waxy solid (11.1 g, 100%). MS (m/z): 212 (M-Br).

Preparation 11

1-Benzyl-4-isopropyl-3,6-dihydro-2H-pyridine

Add sodium tetrahydroborate (1.8 g, 47.4 mmol) in portions to a solution of 1-benzyl-4-isopropyl-pyridin-1-ium bromide (11.1 g, 36.5 mmol) in EtOH (55 mL) at 0° C. Allow the reaction mixture to reach ambient temperature slowly and stir overnight. Add 10 mL of water and remove the organic solvent under vacuum. Add water and then adjust the pH with HCl (5M) to a pH of 1-2. Stir the mixture for 15 min and then add NaOH (2M) until the pH is 8-9. Extract the aqueous layer with EtOAc, combine the organic layers; and sequentially wash with NaOH (2M) then brine. Dry the organic over anhydrous sodium sulphate; filter; and concentrate the filtrate. Purify the compound by chromatography on a silica gel cartridge eluting with hexane:ethyl acetate (9:1, 7:3, 5:5, and then 100% ethyl acetate) to obtain the title compound as a pale yellow oil (6.7 g, 83%). MS (m/z): 216 (M+1).

Preparation 12

Trans-1-benzyl-4-isopropyl-piperidin-3-ol

Add boron trifluoride etherate (4.6 mL, 36.2 mmol) slowly to a solution of 1-benzyl-4-isopropyl-3,6-dihydro-2H-pyridine (6.7 g, 30.2 mmol) in anhydrous tetrahydrofuran (15 mL) at 0° C. under a nitrogen atmosphere. Stir the mixture for 15 minutes and then dropwise add borane-tetrahydrofuran complex (1M in tetrahydrofuran, 42.3 mL, 42.2 mmol). Allow the mixture to reach ambient temperature and stir for 6 hours. Then add slowly borane-tetrahydrofuran complex (24.1 mL, 24.1 mmol) and stir the mixture overnight. Cool the mixture at 0° C. and add methanol (54 mL) slowly. Stir the mixture at ambient temperature for one hour. Cool the mixture to 0° C. and add a solution of 10% $CaCl_2$ in HCl (0.2M) slowly until the mixture has a pH of 1-2. Stir the mixture at ambient temperature for 1.5 hours. Cool the mixture at 0° C. and add a solution of 35% hydrogen peroxide (3.1 mL, 36.2 mmol). Stir the mixture at ambient temperature over the weekend. Add an aqueous solution of 10% $Na_2SO_3$ (15 mL) and methyl tert-butyl ether (50 mL). Add NaOH (5M) to pH 11-12. Separate the organic layer and extract the aqueous layer with methyl tert-butyl ether. Combine the organic layers and wash with brine; dry over $MgSO_4$; filter; collect the filtrate; then remove the solvent under vacuum. Purify the residue by chromatography on a silica gel cartridge eluting with hexane:ethyl acetate (100% to 50% hexane) to obtain the title compound (2.6 g, 37%). MS (m/z): 234 (M+1).

Preparation 13

Trans-1-benzyl-4-ethyl-piperidin-3-ol

Trans-1-benzyl-4-ethyl-piperidin-3-ol is prepared essentially by the method of Preparation 12. MS (m/z): 220 (M+1).

Preparation 14

Trans-tert-butyl 3-hydroxy-4-isopropyl-piperidine-1-carboxylate

Charge a Fisher-Porter reactor with trans-1-benzyl-4-isopropyl-piperidin-3-ol (2.6 g, 11.1 mmol), di-t-butyldicarbonate (2.7 g, 12.3 mmol), palladium hydroxide on carbon (20% Pd, moisture 60%, 1.0 g, 7.1 mmol), EtOH (10 mL) and triethylamine (1.7 mL, 12.3 mmol). Stir the mixture at ambient temperature under hydrogen atmosphere (70 psi) overnight. Evacuate the excess of hydrogen and filter the mixture through a pad of Celite®. Concentrate the filtrate. Add methyl tert-butyl ether to the residue and sequentially wash with water and brine. Dry the organic layer over anhydrous sodium sulphate, filter; collect the filtrate and remove the solvent to obtain the title compound as a waxy solid (2.2 g, 81%). MS (m/z): 188 (M-tBu+1).

Preparation 15

Trans-tert-butyl 4-ethyl-3-hydroxy-piperidine-1-carboxylate

Trans-tert-butyl 4-ethyl-3-hydroxy-piperidine-1-carboxylate is prepared essentially by the method of Preparation 14. MS (m/z): 174 (M-tBu+1).

Preparation 16

Trans-tert-butyl 3-ethoxy-4-isopropyl-piperidine-1-carboxylate

Add sodium hydride (69 mg, 1.73 mmol) to a solution of trans-tert-butyl 3-hydroxy-4-isopropyl-piperidine-1-carboxylate (300 mg, 1.23 mmol) in anhydrous DMF (2.5 mL) at ambient temperature. Stir the mixture for 25 minutes and then add iodoethane (112 μL, 1.48 mmol). Stir the mixture overnight. Add additional iodoethane (59.3 μL, 0.74 μmol) and stir the mixture for 3 h, then add water. Extract the aqueous layer with EtOAc, combine the organic layers. Sequentially wash the combined organic layers with water then brine; dry over anhydrous sodium sulphate; filter; collect the filtrate; and then remove the solvent under vacuum. Purify the compound by silica gel chromatography eluting with hexane: ethyl acetate (0%, 2%, 4% and 6% ethyl acetate) to obtain the title compound as a waxy solid (260 mg, 78%). MS (m/z): 216 (M-tBu+1)

Preparation 17

Trans-tert-butyl-4-ethyl-3-(2,2,2-trifluoroethoxy) piperidine-1-carboxylate

Add a solution of sodium nitrite (1.8 g, 26.2 mmol in water (7.0 mL) dropwise at ambient temperature to a solution of 2,2,2-trifluoroethylamine hydrochloride (2.9 g, 20.9 mmol) in water (1.7 mL) under nitrogen atmosphere in a 25 mL round bottom flask connected via cannula tube with another round bottom flask containing a solution of trans-tert-butyl 4-ethyl-3-hydroxy-piperidine-1-carboxylate (400 mg, 1.74 mmol), tetrakis(acetato)dirhodium(II) (78 mg, 0.17 mmol) and 500 mg of molecular sieves (3 Å) in DCM (17 mL) under nitrogen atmosphere. Stir the mixture at ambient temperature for 2 hours; filter the mixture; and concentrate the filtrate. Purify the compound by chromatography in a silica gel cartridge eluting with DCM to obtain the title compound as a pale brown waxy solid (140 mg, 75% pure by $^1$HNMR and can be used without further purification). MS (m/z): 256 (M-tBu+1).

Preparation 21

5-Phenyl-1,2,3,6-tetrahydropyridine

Add slowly (over 70 min) a solution of N-Boc-3-Piperidone (494.35 mmol; 98.50 mL; 98.50 g) in anhydrous THF (118.20 mL) to a suspension of 1M phenyl magnesium bromide in THF (593.22 mmol; 593.22 mL; 593.22 g) at 0° C. under nitrogen. Stir the mixture at 0° C. for 1.5 h. Then, add slowly trifluoroacetic acid (593.22 mmol; 44.86 mL). Concentrate partially the mixture removing about 450 mL of solvent to give brown oil and stir at 22° C. for 1 h. Then, add trifluoroacetic acid (9.81 moles; 741.53 mL) to this residue at 10° C. Stir the mixture at 22° C. for 15 min to give a red solution. Then, warm the red solution at 75° C. for 2 h and cool slowly to 22° C. for 18 h. Concentrate the mixture. Add an aqueous solution (50%) of NA OH (3.46 moles; 266.17 mL) to the resulting brown suspension at −20° C. Dilute the suspension with water (1 L) and EtOAc (3 L) and concentrate. Filter the brown suspension and concentrate the mother liquors to give a brown solution. Extract this solution with DCM (5×800 mL) and concentrate the organic layers. Filter the aqueous layer through CELITE® and separate the filtrates. Concentrate all the combined organics to give the title compound as brown oil (103.1 g, 98%). MS (m/z): 160 (M+1).

Preparation 22 tert-Butyl 5-phenyl-3,6-dihydro-2H-pyridine-1-carboxylate

Add di-t-butyldicarbonate (728.42 mmol; 158.98 g) to a solution of 5-phenyl-1,2,3,6-tetrahydropyridine (103.1 g, 485.62 mmol) in 1,4-dioxane (971.23 mL) at 2° C. and stir the mixture at 22° C. for 16 hours. Stir the mixture at ambient temperature for 10 min. Concentrate the dark brown mixture and dilute the residue with water (500 mL). Extract the mixture with MTBE (2×500 mL), and wash the dark brown organics with water (2×200 mL), and brine (2×200 mL), filter through a pad of CELITE® and concentrate the filtrates. Purify the residue by isco system (1500 g column; eluent: hexane/EtOAc 9:1; 0.5 L fractions, charge in DCM) and repurify by isco system (700 g TITAN® column; eluent: hexane/EtOAc 100:0 to 90:10; 0.5 L fractions, charge in heptane) to give the title compound as a white solid (36.2, 28%). MS (m/z): 204 (M-tBu+1), 160 (M-Boc+1).

Preparation 24

(−)tert-Butyl trans 4-hydroxy-3-phenyl-piperidine-1-carboxylate

Add slowly over 35 minutes a 1M solution of borane tetrahydrofuran complex (137.35 mmol; 137.35 mL) to a solution of tert-butyl 5-phenyl-3,6-dihydro-2H-pyridine-1-carboxylate (137.35 mmol; 36.20 g) in anhydrous THF (362.00) at 0° C. under nitrogen and warm the mixture to 22° C. for 18 h. Then, add slowly a 2M aqueous solution of NaOH (54.94 mmol; 27.47 mL) at 0° C. and stir the mixture for 5 min. Add a 35% aqueous solution of hydrogen peroxide (274.70 mmol; 23.88 mL) at 0° C. and stir the mixture at 22° C. for 2 h, dilute with water (300 mL). Dilute the mixture with EtOAc (250 mL) and separate the organic layer. Extract the aqueous layer with EtOAc (250 mL). Wash the combined organic layers with sodium bisulfate (214.39 mL) and concentrate. Purify the residue by flash chromatography (750 g column; eluent: hexane/EtOAc 80:20 to 60:40; 400 mL fractions, charge in DCM (100 mL)) and then by chiral chromatography Chiralpak AD, 20 um, 8×25 cm; mobile phase: Isocratic 100% MeOH-0.2% DMEA Flow rate: 300 ml/min UV detection: 225 nm Loading: 3 g/6 min. Collect the first eluting isomer to give the title compound (11.85 g, 31%). MS (m/z): 222 (M-tBu+1) [Alpha]Na=−22.89 (in methanol, 25° C.)

Preparation 25

Trans-tert-butyl 4-methoxy-3-phenyl-piperidine-1-carboxylate

Add sodium hydride (2.19 g, 54.75 mmol) in one portion to a solution of (−)trans-tert-butyl 4-hydroxy-3-phenyl-piperidine-1-carboxylate (11.8 g, 42.12 mmol) in DMF (168.5 mL) at 0° C. under a nitrogen atmosphere. Stir the mixture for 30 min and then add methyl iodide (3.15 mL, 50.54 mmol) dropwise. Stir the mixture at 0° C. for 1 minute and warm to 22° C. for 1 hour. Add additional sodium hydride (303 mg, 12.6 mmol), stir for 15 min, and then add methyl iodide (0.52 mL, 8.4 mmol) slowly. Stir the mixture at 22° C. for 1 hour, cool to 0° C. for 1 hour and add water (118 mL) carefully. Filter the resulting suspension, rinse the solid with water and dry the solid in the vacuum oven (45° C., 60 mbar) to obtain the title compound as a white solid (12.5 g, 99%). MS (m/z): 192 (M-Boc+1), 236 (M-tBu+1).

Preparation 26

3-Bromo-2-methoxy-6-methylpyridine

To a cooled (0° C.) solution of 3-bromo-2-chloro-6-methylpyridine (300 mg, 1.45 mmol) in tetrahydrofuran (20 mL), add sodium methoxide (1.57 g, 29 mmol), slowly with stirring. Allow the mixture to warm to ambient temperature and stir overnight. Add additional sodium methoxide (500 mg) and stir at 100° C. overnight. Quench with water (20 mL), extract three times with ethyl acetate (30 mL). Combine the organics and wash with water then brine, and dry over sodium sulphate. Filter and concentrate to give the title product as a yellow solid (135 mg, 46%). $^1$HNMR (MeOH-d$_4$): δ 7.72 (d, 1H), 6.70 (d, 1H), 3.93 (s, 3H), 2.38 (s, 3H).

Preparation 27

2-(Benzyloxy)-6-chloropyridine

Add benzyl bromide (1 mL, 8.38 mmol) to a solution of 6-chloropyridin-2-ol (2 g, 15.4 mmol), potassium carbonate (3.41 g, 24.7 mmol) in DMF (20 mL) heat to 80° C. and stir for two hours. Quench reaction mixture with water, then extract three times with 20 mL EtOAc. Combine the organic washings and wash with water (20 mL); dry over sodium sulphate; filter; collect the filtrate; and concentrate under vacuum. Purify via normal phase silica gel flash column chromatography using a gradient of 0-50% ethyl acetate in petroleum ether to give the title compound as a clear oil. MS: (m/z): 220 (M+1).

Preparations 28-29 are prepared essentially by the method of preparation 27

TABLE 1

| Prep # | Chemical name | Physical data |
|---|---|---|
| 28 | 2-Chloro-6-isopropoxy-pyridine | $^1$HNMR (CDCl$_3$-d): δ 7.46(t, 1H), 6.81(d, 1H), 6.56(d, 1H), 5.26-5.30(m, 1H), 1.32(s, 6H). |
| 29 | 2-Chloro-6-ethoxy-pyridine | $^1$HNMR (CDCl$_3$-d): δ 7.47(t, 1H), 6.84(d, 1H), 6.60(d, 1H), 4.31-4.33(m, 2H), 1.36(t, 3H). |

Preparation 30 tert-Butyl 6-(benzyloxy)-3',6'-dihydro-2,4'-bipyridine-1'(2'H)-carboxylate

To a flask equipped with an N$_2$ inlet adaptor, add 2-(benzyloxy)-6-chloropyridine (1.63 g, 7.42 mmol), tert-butyl 4-(4,4,5,5-tetramethyl-1,3,2-dioxaborolan-2-yl)-5,6-dihydropyridine-1(2H)-carboxylate (2.3 g, 7.42 mmol), tris(dibenzylideneacetone)dipalladium(0) (339.5 mg, 371.0 μmol), potassium phosphate (3.94 g, 18.55 mmol), tricyclohexylphosphine (208 mg, 0.742 mmol), water (4 mL) and 1,4-dioxane (40 mL). Flush with N$_2$, then heat the mixture at 95° C. overnight under a nitrogen atmosphere. Filter and concentrate under vacuum to give a residue. Purify via silica gel flash column chromatography using a gradient of 0-30% ethyl acetate in petroleum ether to give the title compound as a white solid (2.6 g, 95.6%). MS (m/z): 367 (M+1).

Preparations 31-36 are prepared essentially by the method of preparation 30:

TABLE 2

| Prep # | Chemical name | Physical data MS (m/z) |
|---|---|---|
| 31 | tert-Butyl 6-(1-methylethoxy)-3',6'-dihydro-2,4'-bipyridine-1'(2'H)-carboxylate | 319 (M + 1). |

TABLE 2-continued

| Prep # | Chemical name | Physical data MS (m/z) |
|---|---|---|
| 32 | tert-Butyl 6-ethoxy-3',6'-dihydro-2,4'-bipyridine-1'(2'H)-carboxylate | 305 (M + 1). |
| 33 | tert-Butyl 2-methoxy-6-methyl-3',6'-dihydro-3,4'-bipyridine-1'(2'H)-carboxylate | 305 (M + 1). |
| 34 | tert-Butyl 4-(4-fluorophenyl)-3,6-dihydro-2H-pyridine-1-carboxylate | 196 (M + 1-Boc) |
| 35 | tert-Butyl 6-fruoro-3',6'-dihydro-3,4'-bipyridine-1'(2'H)-carboxylate | 279(M + 1) |
| 36 | tert-Butyl 4-(2-ethoxy-4-fruorophenyl)-3,6-dihydropyridine-1(2H)-carboxylate | 266 (M + 1-tBu) |

Preparation 37 tert-Butyl 4-(6-hydroxypyridin-2-yl)piperidine-1-carboxylate

Add Pd/C (5 wt/wt %, 0.26 g, 0.12 mmol) to a solution of tert-butyl 4-(6-(benzyloxy)pyridin-2-yl)-5,6-dihydropyridine-1(2H)-carboxylate (2.6 g; 7.1 mmol) in methanol (20 mL) add Pd/C (5 wt/wt %, 0.26 g, 0.12 mmol) and stir overnight under a hydrogen balloon. Filter and concentrate under vacuum to give the crude product. Purify with normal phase silica gel flash column chromatography, using a gradient of 0-20% MeOH in DCM to give the title product as a white solid (1.2 g, 615). MS (m/z): 223 (M-t-Bu+1).

Preparations 38-41 are prepared essentially by the method of preparation 37.

TABLE 3

| Prep # | Chemical name | Physical data |
|---|---|---|
| 38 | tert-Butyl 4-[6-(1-methylethoxy)pyridin-2-yl]piperidine-1-carboxylate | MS (m/z): 318 (M + 1). |
| 39 | tert-Butyl 4-(6-ethoxypyridin-2-yl)piperidine-1-carboxylate | MS (m/z): 307 (M + 1). |
| 40 | tert-Butyl 4-(2-methoxy-6-methylpyridin-3-yl)piperidine-1-carboxylate | MS (m/z): 307 (M + 1) |
| 41 | tert-butyl 4-(2-ethoxy-4-fluorophenyl)piperidine-1-carboxylate | MS (m/z): 268 (M + 1-tBu) |

Preparation 42 tert-Butyl 4-(6-(cyclopropylmethoxy)pyridin-2-yl)piperidine-1-carboxylate

Stir tert-butyl 4-(6-hydroxypyridin-2-yl)piperidine-1-carboxylate (0.25 g, 0.90 mmol) in DMF (10 mL) and add cesium carbonate (0.44 g, 1.35 mmol) and (bromomethyl)cyclopropane (0.13 g, 0.99 mmol). Heat the mixture to 30° C. and stir overnight. Quench the reaction with water, and extract three times with EtOAc (20 mL). Combine the organic extracts. Wash the extracts with water then brine; dry over sodium sulphate; collect the filtrate; and concentrate under vacuum to give the crude product. Purify using silica gel normal phase flash column chromatography using a gradient of 0-30% ethyl acetate in petroleum ether to give the title compound (0.28 g, 94%) as a clear oil. MS (m/z): 333 (M+1).

Preparation 43 tert-butyl-(3R,4R)-4-(4-fluorophenyl)-3-hydroxy-piperidine-1-carboxylate

Add borane tetrahydrofuran complex (171 mL, 171 mmol) to a solution of tert-butyl 4-(4-fluorophenyl)-3,6-dihydro- 2H-pyridine-1-carboxylate (54 g, 186 mmol) in THF (544 mL) under a nitrogen atmosphere. Stir overnight at 40° C., then add 2M sodium hydroxide (36.8 g, 70.8 mmol) and stir for 12 minutes at ambient temperature. Add hydrogen peroxide (31.1 mL, 357.8 mmol) while maintaining the internal temperature at 19-21° C. through the use of an ice-water bath. After addition is complete, remove the ice bath and stir at ambient temperature for 3 hours. Dilute the reaction mixture with water (250 mL) and extract twice with methyl tert-butyl ether (500 mL). Combine organic extracts, and sequentially wash with brine, sodium bisulfate then brine again. Dry the organics over magnesium sulphate; filter; collect the filtrate; and concentrate under vacuum. Purify the crude material via flash column chromatography using hexane/ethyl acetate (4:1, then 3:1) followed by DCM/EtOAc (1:1, then 0:100). Combine product fractions and dry under vacuum to give a white solid. Separate enantiomers using chromatography conditions "L" (see below), collecting the first eluting isomer to give the title compound (20.02 g, 36.4%) as a white solid. MS (m/z): 196 (M+1-Boc).

Preparation 44 tert-butyl Trans-4-(6-fluoro-3-pyridyl)-3-hydroxy-piperidine-1-carboxylate tert-butyl trans-4-(6-fluoro-3-pyridyl)-3-hydroxy-piperidine-1-carboxylate is prepared essentially by the method of Preparation 43 with the exception of use of chiral chromatography to the instant racemate. MS (m/z): 279 (M+1)

Preparation 45 tert-butyl-(3R,4R)-4-(4-fluorophenyl)-3-methoxy-piperidine-1-carboxylate

Dissolve tert-butyl-(3R,4R)-4-(4-fluorophenyl)-3-hydroxy-piperidine-1-carboxylate (496 mg, 1.51 mmol) in THF (3 mL) and cool to 0° C. in an ice water bath. Add sodium hydride (84.6 mg, 2.12 mmol), stir for 30 min, and then add methyl iodide (141 uL, 2.27 mmol). Warm to ambient temperature and stir for 5 hours. Quench the reaction with water (5 mL) and separate layers. Extract aqueous layer three times with methyl tert-butyl ether (8 mL), combine organic extracts; dry over magnesium sulphate; filter; collect the filtrate; and concentrate under vacuum to give the title product as a yellow oil (525 mg, 99.9%). MS (m/z): 210 (M+1-Boc). The Preparations 46-47 are prepared essentially by the method of Preparation 45.

TABLE 4

| Prep # | Chemical name | Physical data |
|---|---|---|
| 46 | tert-Butyl trans-3-ethoxy-4-(6-fluoro-3-pyridyl)piperidine-1-carboxylate | MS (m/z): 269 (M + 1-tBu) |
| 47 | tert-Butyl trans-3-ethoxy-4-(4-fruorophenyl)piperidine-1-carboxylate | MS (m/z): 222 (M-Boc) |

Preparation 48 tert-Butyl trans-3-(difluoromethoxy)-4-(4-fluorophenyl)piperidine-1-carboxylate

Dissolve trans-tert-butyl-4-(4-fluorophenyl)-3-hydroxy-piperidine-1-carboxylate (0.9 g, 3.1 mmol) and copper(I) iodide (116 mg, 609 mmol) in ACN (7.6 mL) and heat to 50° C. Add fluorosulfonyldifluoroacetic acid (336.7 mg, 1.83 mmol) dropwise over 15 minutes. Stir the solution for 2 hours at 50° C. and then cool to ambient temperature. Quench with a 50% solution of sodium bicarbonate; separate layers; and extract the aqueous layer twice with EtOAc. Combine the organic extracts; dry over sodium sulfate; filter; collect the filtrate; and concentrate under vacuum. Purify the crude material with silica gel flash column chromatography, with a gradient of 0-20% EtOAc in hexane to give the title compound (0.18 g, 17%). 1H-NMR ($d_6$-DMSO) δ 0.74 (s, 1H), 1.42 (s, 9H), 1.5-1.79 (m, 2H), 2.6-2.85 (m, 2H), 3.59-4.82 (m, 4H), 6.4 (dd, J=76.8 Hz, 77.9 Hz, 1H), 7.0-7.1 (m, 2H), 7.27-7.33 (m, 2H).

Preparation 49 tert-Butyl 4-oxo-3-(thiazol-2-yl)piperidine-1-carboxylate

Add sodium hydride (3.61 g, 90.3 mmol) to a solution of tert-butyl 4-oxopiperidine-1-carboxylate (12.0 g, 60.2 mmol) and stir for one hour at ambient temperature. Add 2-chlorothiazole (7.92 g, 66.3 mmol) and stir one additional hour at ambient temperature. Heat to reflux and stir for 14 hours at reflux. Cool mixture to ambient temperature and quench with sufficient HCl (2N) to adjust the pH of the mixture to less than 5. Extract the mixture three times with EtOAc; combine the organic extracts; sequentially wash with water then brine; dry over magnesium sulphate; filter; collect the filtrate; and then concentrate under vacuum at 40° C. Purify the crude material by silica gel flash column chromatography eluting with 10% EtOAc in hexane to give the title compound as a white solid (4.0 g, 23.5%). $^1$HNMR ($d_6$-DMSO) δ 1.3 (s, 9H), 2.3-2.5 (m, 2H), 3.5 (t, J=6.1 Hz, 2H), 4.1-4.3 (m, 3H), 7.5 (s, 1H), 7.7 (s, 1H).

Preparation 50 tert-butyl trans-4-hydroxy-3-thiazol-2-yl-piperidine-1-carboxylate

Add sodium tetraborohydride (535.9 mg, 14.2 mmol) to a solution of tert-butyl 4-oxo-3-(thiazol-2-yl)piperidine-1-carboxylate (4.0 g, 14.2 mmol) in MeOH (175 mL) and stir at ambient temperature for 45 minutes. Quench the reaction mixture with water (100 mL). Concentrate under vacuum to remove MeOH. Extract the aqueous residue with EtOAc (3×100 mL), combine the organic extracts and sequentially wash with water (100 mL) then brine (100 mL). Dry over sodium sulphate; filter; collect the filtrate; and concentrate under vacuum to give the title compound as a mixture of diastereomer pairs (3.9 g). MS (m/z): 285 (M+1).

Separate the mixture using silica gel flash column chromatography, with a gradient of 20-100% EtOAc in hexane. Collect the second eluting isomer to give the compound 3,4-trans-tert-butyl-4-hydroxy-3-thiazol-2-yl-piperidine-1-carboxylate (1.4 g, 33.5%) as a white solid. MS (m/z): 285 (M+1).

The undesired cis-isomer can be recovered and efficiently converted to the desired trans-isomer. Add potassium tert-butyoxide (19.7 g 170.28 mmol) in four portions to a solution of racemic 3,4-cis-tert-butyl-4-hydroxy-3-thiazol-2-yl-piperidine-1-carboxylate (24.2 g, purity 87%, 74.04 mmol) in anhydrous THF (370 mL) at 0° C. under nitrogen atmosphere. Remove the ice-bath and stir the mixture for 30 min. Add water at room temperature and separate the organic layer.

Extract the aqueous layer with EtOAc. Combine the organic layers, dry over anhydrous sodium sulphate, filter, collect the filtrate, and remove the solvent under vacuum. Purify the compound by chromatography in the varian (cartridge: SF65-400 g) eluting with DCM:EtOAc (20% to 50% 1V, then 50% 2V, 50% to 100% 1V, and then 100% 2V) to obtain the title compound as a white solid (14 g, 66% yield). MS (m/z): 285 (M+1), 229 (M-tBu+1).

Preparation 51 tert-Butyl trans-4-methoxy-3-thiazol-2-yl-piperidine-1-carboxylate

Add sodium hydride (1.07 g, 26.7 mmol) in four portions to 0° C. solution of 3,4-trans-tert-butyl-4-hydroxy-3-thiazol-2-yl-piperidine-1-carboxylate (4.75 g, 16.7 mmol) in anhydrous dimethylformamide (50 mL). Stir at 0° C. for 5 minutes, then add methyl iodide (2.37 g, 16.7 mmol) dropwise over 10 minutes. Stir for 30 minutes then add water to quench the reaction. Extract it with EtOAc, combine organic extracts and sequentially wash with water then brine; dry over anhydrous sodium sulphate; filter; collect the filtrate; then concentrate under vacuum to give the title compound as a racemic mixture (4.85 g, 97.3%) as a white solid. MS (m/z): 299 (M+1).

Preparation 52 tert-Butyl 4-(cyclopropylcarbonyl)piperidine-1-carboxylate

Add cyclopropylmagnesium bromide (4.8 g, 33.0 mmol) to a solution of tert-butyl 4-(methoxy(methyl)carbamoyl)piperidine-1-carboxylate (7.5 g, 27.5 mmol) in tetrahydrofuran (120 mL) at 0° C. Remove the cooling bath and stir at ambient temperature overnight. Add an additional cyclopropylmagnesium bromide (20 mL) and stir an additional 4 hours. Pour into a solution of saturated sodium bicarbonate and extract once with diethyl ether and once with EtOAc. Combine organic extracts, dry over sodium sulphate; filter; collect the filtrate; and concentrate under vacuum. Purify via flash column chromatography using a gradient of 0-40% ethyl acetate in hexane to give the title compound (6.4 g, 91.7%). MS (m/z): 198 (M+1-tBu).

Preparation 53 tert-Butyl 4-(1-cyclopropylethenyl)piperidine-1-carboxylate

Dissolve methyltriphenylphosphonium bromide (20.26 g, 55.6 mmol) in THF (200 mL) and cool to −78° C. Add butyllithium (20.2 mL, 50.5 mmol) and stir at −78° C. for 15 minutes. Warm to ambient temperature and add a solution of tert-butyl 4-(cyclopropylcarbonyl)piperidine-1-carboxylate in THF (5 mL) dropwise. Stir the mixture overnight at ambient temperature. Quench with 50% saturated sodium bicarbonate solution, extract twice with diethyl ether and twice with EtOAc. Combine the organic extracts; wash with brine; dry over sodium sulphate; collect the filtrate; and concentrate under vacuum. Add a mixture of 1:1 diethyl ether:hexane (20 mL) and filter. Concentrate the filtrate under vacuum and purify via flash column chromatography to give the title compound (5.3 g, 83.5%). MS (m/z): 196 (M+1-tBu)

Preparation 54 tert-Butyl 4-(1-cyclopropylethyl)piperidine-1-carboxylate

Add ruthenium dioxide monohydrate (2.0 g, 15.0 mmol) to a 500 mL Parr shaker bottle and wet with isopropyl alcohol (25 mL). Add tert-butyl 4-(1-cyclopropylethenyl)piperidine-1-carboxylate (3.8 g, 15.1 mmol) and isopropyl alcohol (100 mL) and place on Parr shaker. React under $H_2$ atmosphere (30 psi) at ambient temperature for a total of 12 hours. Vent and purge the bottle, filter and concentrate in vacuo to give the title compound as a clear oil (3.55 g, 92.9%). MS (m/z): 198 (M+1-tBu)

Preparation 55

2-[Trans-4-methoxy-3-piperidyl]thiazole

Stir tert-butyl trans-4-methoxy-3-thiazol-2-yl-piperidine-1-carboxylate (4.8 g, 16.1 mmol) in dichloromethane (80.4 mL) and add trifluoroacetic acid (7.30 mL, 96.51 mmol). Stir the mixture at ambient temperature overnight. Remove the solvent under reduced pressure, and purify the residue via SCX (50 g cartridge) eluting with 2N $NH_3$/MeOH. Concentrate the appropriate fractions under reduced pressure to give the title compound (3.2 g, 85.3%) as a waxy solid. MS (m/z): 199 (M+1).

The Preparations 56-65 are prepared essentially by the method of Preparation 55

TABLE 5

| Prep # | Chemical name | Physical data MS (m/z) |
|---|---|---|
| 56 | 2-(1-Methylethoxy)-6-piperidin-4-ylpyridine | 221 (M + 1). |
| 57 | 2-Ethoxy-6-(piperidin-4-yl)pyridine | 207 (M + 1). |
| 58 | 2-Methoxy-6-methyl-3-piperidin-4-ylpyridine | 207 (M + 1) |
| 59 | Trans-5-[3-ethoxypiperidin-4-yl]-2-fluoropyridine | 225(M + 1) |
| 60 | Trans-3-(difluoromethoxy)-4-(4-fluorophenyl)piperidine | 246(M + 1) |
| 61 | Trans-3-ethoxy-4-isopropyl-piperidine | 172 (M + 1) |
| 62 | Trans-4-ethyl-3-(2,2,2-trifluoroethoxy)piperidine | 212 (M + 1) |
| 63 | 4-(1-cyclopropylethyl)-piperidine | 154(M + 1) |
| 64 | 2-(Cyclopropylmethoxy)-6-(piperidin-4-yl)pyridine | 223 (M + 1) |
| 65 | (3R,4R)-4-(4-Fluorophenyl)-3-methoxypiperidine | 210 (M + 1) |

Preparation 66

4-(2-Ethoxy-4-fluorophenyl)piperidine hydrochloride

Dissolve tert-butyl 4-(2-ethoxy-4-fluoro-phenyl)piperidine-1-carboxylate (3.5 g, 10.8 mmol) in DCM (28 mL) and add HCl (4M solution in dioxanes, 27 mL, 108.2 mmol). Stir at ambient temperature for 4 hours, and then concentrate to dryness under vacuum. Triturate with diethyl ether to give a racemic mixture of the title compound as a white solid (2.4 g, 85.4%). MS (m/z): 223 (M-HCl)

Preparation 67

Trans-4-methoxy-3-phenyl-piperidine hydrochloride

Trans-4-methoxy-3-phenyl-piperidine hydrochloride is prepared essentially by the method of Preparation 66. MS (m/z): 192 (M+1).

Preparation 68

Benzyl 4-(1-cyclopropylethyl)piperidine-1-carboxylate

Dissolve racemic 4-(1-cyclopropylethyl)-piperidine (1.75 g, 11.42 mmol) and N,N-dimethyl-4-pyridinamine (139.5 mg, 1.14 mmol) in pyridine (15 mL) and dichloromethane (30 mL). Add N-(benzyloxycarbonyloxy)succinimide (3.70 g, 14.84 mmol) and stir the solution for 4 hours. Pour the reaction mixture into 5N HCl and extract twice with EtOAc. Wash the organic extracts with sodium bicarbonate, followed by brine; dry over sodium sulfate; filter; collect the filtrate; and concentrate under reduced pressure. Purify the crude material on a silica gel flash column chromatography using a gradient of 0-20% EtOAc in hexane to give the title compound (3.0 g, 91%) as a clear oil. MS (m/z): 288 (M+1).

Preparations 69 and 70

Enantiomers of benzyl 4-(1-cyclopropylethyl)piperidine-1-carboxylate isomer 1 (Preparation 69); isomer 2 (Preparation 70)

Purify racemic benzyl 4-(1-cyclopropylethyl)piperidine-1-carboxylate (3.9 g, 13.57 mmol, from 3 lots of combined material) with chiral chromatography according to condition P below in Table 7 to give the two title compounds isomer 1 (the first eluting isomer, 1.80 g, 46.2%) and isomer 2 (the second eluting isomer, 1.77 g, 45.4%). MS (m/z): 288 (M+1).

Preparation 71

4-(1-Cyclopropylethyl)-piperidine, Isomer 1

Dissolve benzyl 4-(1-cyclopropylethyl)piperidine-1-carboxylate, isomer 1 (1.8 g, 6.26 mmol) in EtOAc (30 mL). Add palladium on carbon (5%, 200 mg, 0.09 mmol) and stir under a hydrogen atmosphere (40 psi) for one hour. Filter and concentrate under vacuum. Purify the residue with SCX column eluting with 2M NH$_3$/MeOH to provide the title compound (850 mg, 88.6%). MS (m/z):154 (M+1).

Preparation 72

4-(1-cyclopropylethyl)-piperidine, Isomer 2

4-(1-cyclopropylethyl)-piperidine, Isomer 2 is prepared essentially by the method of Preparation 71. MS (m/z): 154 (M+1).

Preparation 73

Phenyl 4-cyclobutylpyridine-1(4H)-carboxylate

Mix pyridine (3.0 mL, 37.5 mmol), copper cyanide (0.23 g, 2.50 mmol) and lithium bromide (0.44 g, 5.0 mmol) in THF (100 mL) at ambient temperature. Add phenyl carbonochloridate (3.91 g, 25.0 mmol) dropwise, and stir the mixture for 15 minutes. Add bromo(cyclobutyl)zinc (50 mL, 25.0 mmol) dropwise, and stir the mixture for 5 hours at ambient temperature. Add NaHCO$_3$ (aq.) and 100 mL diethyl ether. Separate layers and extract the aqueous portion twice more with diethyl ether. Combine the organic portions and sequentially wash with 20% aqueous NH$_4$Cl, [20% NH$_4$Cl/20% NH$_4$OH (1:1)] then brine; dry over sodium sulfate; filter; and collect the filtrate. Concentrate under reduced pressure to give the title compound (5.6 g, 85.5%). MS (m/z): 256 (M+1).

Preparation 74

Phenyl 4-cyclobutylpiperidine-1-carboxylate

Charge a 500 mL Parr reactor bottle with 10% palladium on carbon (0.56 g, 0.53 mmol) and purge with N$_2$. Wet the catalyst with MeOH (50 mL) and add phenyl 4-cyclobutylpyridine-1(4H)-carboxylate (5.6 g, 21.9 mmol) and an additional 150 mL MeOH. Seal the bottle, purge four times with nitrogen, then four times with hydrogen. Pressurize with hydrogen gas (31 psi) and shake at ambient temperature for two hours. Vent the mixture, purge four times with nitrogen, filter the mixture; collect the filtrate; and then concentrate to remove the MeOH. Purify the crude material with silica gel flash column chromatography eluting with 10% EtOAc in hexane. Concentrate the fractions to give the title compound (2.93 g, 51.5%). MS (m/z): 260.

Preparation 75

4-Cyclobutylpiperidine hydrochloride

Mix potassium tert-butoxide (3.30 g, 28.2 mmol) and THF (37.6 mL) and cool the mixture to −40° C. Add a solution of phenyl 4-cyclobutylpiperidine-1-carboxylate (2.93 g, 11.3 mmol) in THF dropwise. Stir for one hour at −40° C. then overnight at ambient temperature. Quench the reaction mixture with water and dilute with DCM. Adjust the pH of aqueous layer to 13-14, and wash organics with NaOH (1.0 M). Dry the organic layer over sodium sulfate; filter; and collect the filtrate. Add excess amount of 2.0M HCl/diethyl ether and stir for 5 minutes. Concentrate the mixture under reduced pressure, triturate with diethyl ether and filter to obtain the title compound (1.75 g, 88.2%). MS (m/z): 140 (M+1).

EXAMPLE 1

N-[(1S)-1-[4-[(4-tert-Butylpiperidin-1-yl)methyl]phenyl]-2,2,2-trifluoro-ethyl]methanesulfonamide hydrochloride

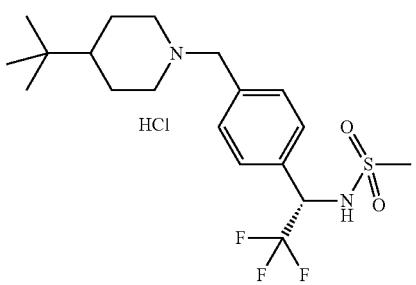 [SMILES: CC(C)(C)C1CCN(Cc2ccc([C@H](NS(C)(=O)=O)C(F)(F)F)cc2)CC1 ; Cl]

Dissolve 4-tert-butylpiperidine hydrochloride (5.0 g, 28.1 mmol) in 150 mL of sodium bicarbonate (saturated aqueous solution), then extract three times with DCM. Combine the organic fractions; dry over sodium sulfate; filter; collect the filtrate; and concentrate under reduced pressure to give 4-tert-butylpiperidine free base. Add N-[(1S)-2,2,2-trifluoro-1-(4-formylphenyl)-ethyl]-methanesulfonamide (7.0 g, 24.9 mmol) to the free base and dissolve the mixture in DCM (150 mL). Stir the mixture at ambient temperature for two hours, and then add sodium triacetoxyborohydride (26.37 g, 124.44 mmol) and acetic acid (1.71 mL, 29.87 mmol). Stir for 72 hours at ambient temperature. Quench the reaction with the addition of 50% saturated sodium bicarbonate solution. Separate the layers, and extract the aqueous layer twice with EtOAc. Combine the organic layers; dry over sodium sulphate; filter; collect the filtrate; and concentrate under reduced pressure. Purify the crude material with silica gel flash column chromatography eluting with MeOH in DCM (0-7%). Collect and concentrate the appropriate fractions under reduced pressure to give the desired compound as a free base (ee>98%). Dissolve the free base in a mixture of MeOH and DCM (1:1, 30 mL). Add HCl (1.0 M in diethyl ether, 40 mL) and swirl the mixture for one minute. Concentrate under reduced pressure to afford the title compound (8.2 g, 74.4%). MS (m/z): 407 (M-HCl+1).

EXAMPLE 2

N-[(1S)-1-{4-[(4-tert-butylpiperidin-1-yl)methyl]phenyl}-2,2,2-trifluoroethyl]methanesulfonamide phosphoric acid

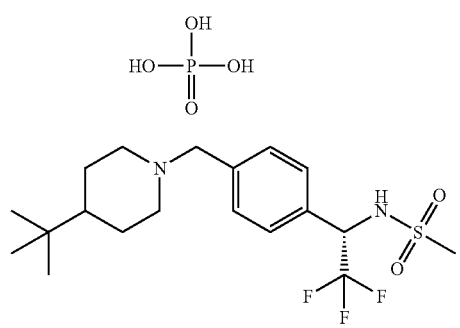

Step 1: Synthesis of N-[(1S)-1-[4-[(4-tert-Butylpiperidin-1-yl)methyl]phenyl]-2,2,2-trifluoro-ethyl]methanesulfonamide Charge a five liter round-bottom flask with DCM (1.5 L) and 4-tert-butylpiperidine hydrochloride (89 g, 0.5 mol). Add triethylamine (101.4 g, 1.0 mol) to the mixture at 21° C. followed by N-[(1S)-2,2,2-trifluoro-1-(4-formylphenyl)ethyl]methanesulfonamide (155 g, 0.55 mol), and acetic acid (36 g, 0.6 mol). Add sodium triacetoxyborohydride (318.6 g, 1.5 mol) portion-wise and stir the suspension at 22° C. for 15 hours. Add saturated aqueous solution of sodium bicarbonate (1800 mL) slowly with stirring until pH of the mixture is 8. Separate the organic layer and extract the aqueous layer with DCM (3×2000 mL). Dry the combined organic layers over MgSO$_4$; filter; collect the filtrate; and concentrate the filtrate under vacuum. Purify the residue on silica gel column chromatography eluting with DCM:MeOH (100 to 95%) to provide the title compound as an off-white solid (126 g, 61.9%). MS (m/z): 407 (M+1).

Step 2: Preparation of seed crystals of N-[(1S)-1-{4-[(4-tert-butylpiperidin-1-yl)methyl]phenyl}-2,2,2-trifluoroethyl]methanesulfonamide phosphate Add a 40 mg/mL solution of N-[(1S)-1-{4-[(4-tert-butylpiperidin-1-yl)methyl]phenyl}-2,2,2-trifluoroethyl]methanesulfonamide (0.25 mL) in acetone to a Freeslate CM3 Crystallizer master slurry plate. Dry under nitrogen. Seal Master plate and run on Freeslate CM3 Crystallizer using the Symyx 8.0.3.351 workflow (Add 0.25M phosphoric acid (1.2 mmol), tumble-stir for 90 minutes at 55° C. Filter the mixture and add 2-propanol (800 uL). Evaporate under nitrogen at ambient temperature to give crystals of N-[(1S)-1-{4-[(4-tert-butylpiperidin-1-yl)methyl]phenyl}-2,2,2-trifluoroethyl]methanesulfonamide phosphate.

Step 3: Preparation of N-[(1S)-1-[4-[(4-tert-Butylpiperidin-1-yl)methyl]phenyl]-2,2,2-trifluoro-ethyl]methanesulfonamide phosphoric acid In a 10 L four-necks round-bottom flask with mechanical stirring, add N-[(1S)-1-[4-[(4-tert-Butylpiperidin-1-yl)methyl]phenyl]-2,2,2-trifluoroethyl]methanesulfonamide (110.17 g, 0.27 mol) to isopropyl alcohol (3100 mL) at 16° C. with stirring. Add crystalline seeds of the phosphate (1.76 g) and the seeds persist in solution. Add a solution of phosphoric acid (2.1 eq, 31.33 mL) in isopropanol (2800 mL) to this solution over two hours. Off white precipitate forms. Then heat the mixture to 80° C. and stir for one hour. During this period a thick white slurry forms. Add more crystalline seeds (1.54 g) and stop the heating. Allow the mixture to reach 12° C. After 14 hours, filter the white slurry off and dry the wet white solid in vacuum oven at 60° C. for 16 hours to provide the title compound as a white solid (122 g, 89.2%). MS (m/z): 407 (M+1-HCl). [α]$_D^{20}$+12.6° (c=2.0, H$_2$O).

The Examples 3-51 are prepared essentially by the method of Example 1. All the following Examples in Table 6 were isolated as single isomers either starting from chiral starting materials and/or using the chromatographic columns and conditions identified below. The separation can be performed with the free base or with its salt form[1].

TABLE 6

| Ex. # | Chemical name | Structure | Physical data MS (m/z): | Chrom Cond. |
|---|---|---|---|---|
| 3 | N-[(1R)-1-{4-[(4-tert-butylpiperidin-1-yl)methyl]phenyl}ethyl]methanesulfonamide hydrochloride | 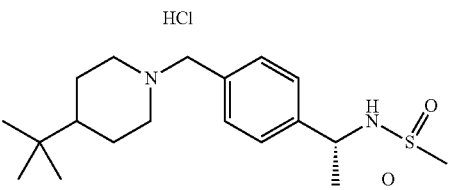 | 353 (M − HCl + 1) | |
| 4 | N-[(1S)-2,2,2-trifluoro-1-(4-{[4-(4-fluorophenyl)piperidin-1-yl]methyl}phenyl)ethyl]methanesulfonamide hydrochloride | 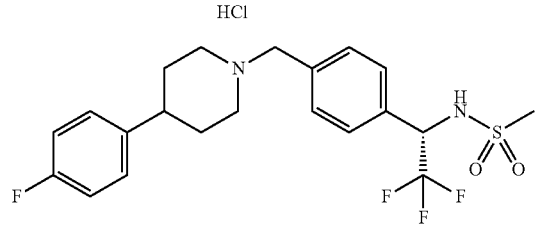 [SMILES: Cl ; CS(=O)(=O)N[C@@H](c1ccc(CN2CCC(c3ccc(F)cc3)CC2)cc1)C(F)(F)F] | 445 (M − HCl + 1) | A |
| 5 | N-[(1R)-1-(4-{[4-(4-fluorophenyl)piperidin-1-yl]methyl}phenyl)ethyl]methanesulfonamide hydrochloride | 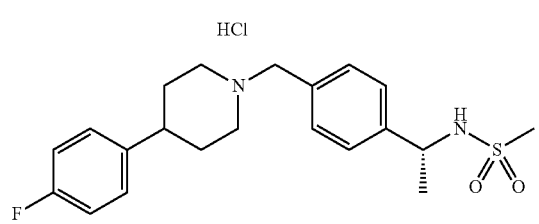 [SMILES: Cl ; C[C@@H](NS(C)(=O)=O)c1ccc(CN2CCC(c3ccc(F)cc3)CC2)cc1] | 391 (M − HCl + 1) | B |
| 6 | Trans-3-ethoxy-4-(1-methylethyl)-1-(4-{(1R)-1-[(methylsulfonyl)amino]ethyl}benzyl)piperidinium chloride | 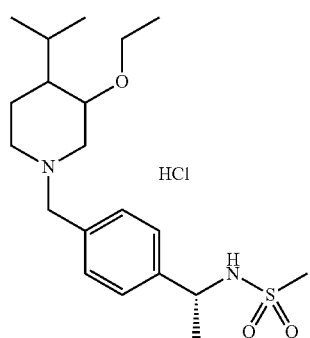   Isomer 2, Trans | 383 (M − HCl + 1) | Q |
| 7 | Trans-4-ethyl-1-(4-{(1R)-1-[(methylsulfonyl)amino]ethyl}benzyl)-3-(2,2,2-trifluoroethoxy)piperidinium chloride | 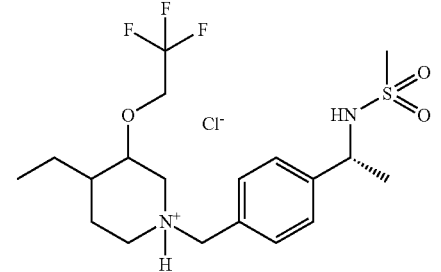   isomer 1 | 423 (M − HCl + 1) | I |

TABLE 6-continued

| Ex. # | Chemical name | Structure | Physical data MS (m/z): | Chrom Cond. |
|---|---|---|---|---|
| 8 | Trans-4-methoxy-1-(4-{(1R)-1-[(methylsulfonyl)amino]ethyl}benzyl)-3-phenylpiperidinium chloride | 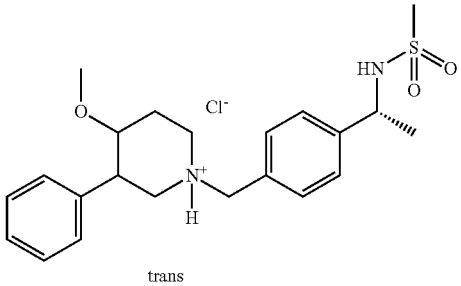 [SMILES: COC1CC[NH+](Cc2ccc([C@@H](C)NS(C)(=O)=O)cc2)CC1c1ccccc1 ; [Cl-]] trans | 403 (M − HCl + 1) | |
| 9 | Trans-N-[(1S)-2,2,2-trifluoro-1-[4-[(4-methoxy-3-phenyl-1-piperidinyl)methyl]phenyl]ethyl]methanesulfonamide hydrochloride. | 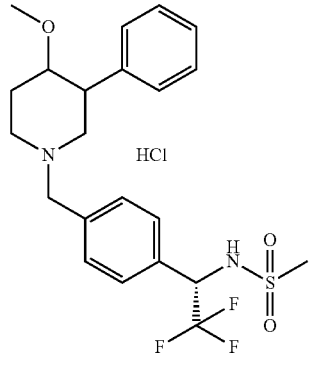 trans | 457 (M − HCl + 1) | |
| 10 | N-[(1R)-1-(4-{[4-(4-chloro-3-fluorophenyl)piperidin-1-yl]methyl}phenyl)ethyl]methanesulfonamide hydrochloride | 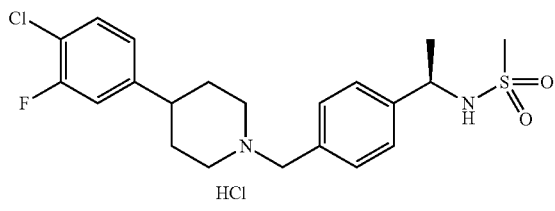 [SMILES: C[C@@H](NS(C)(=O)=O)c1ccc(CN2CCC(c3ccc(Cl)c(F)c3)CC2)cc1 ; Cl] | 425 (M − HCl + 1) | |
| 11 | N-[(1S)-1-{4-[(4-cyclopropylpiperidin-1-yl)methyl]phenyl}-2,2,2-trifluoroethyl]methanesulfonamide hydrochloride | 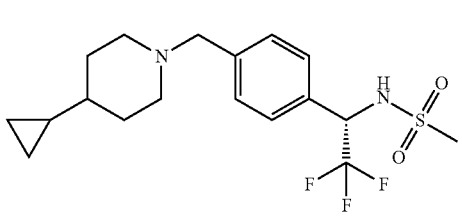 | 391 (M − HCl + 1) | |
| 12 | N-[(1S)-2,2,2-trifluoro-1-(4-{[(3R,4R)-4-(4-fluorophenyl)-3-methoxypiperidin-1-yl]methyl}phenyl)ethyl]methanesulfonamide hydrochloride | 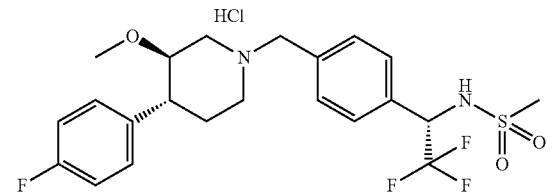 | 475 (M − HCl + 1). | |

TABLE 6-continued

| Ex. # | Chemical name | Structure | Physical data MS (m/z): | Chrom Cond. |
|---|---|---|---|---|
| 13 | N-[(1S)-2,2,2-trifluoro-1-{4-[(3-pyridin-2-yl piperidin-1-yl) methyl]phenyl}ethyl] methane sulfonamide hydrochloride | isomer 1 | 428 (M − HCl + 1) | I |
| 14 | N-[(1S)-2,2,2-trifluoro-1-(4-{[3-(pyridin-3-yl)piperidin-1-yl] methyl}phenyl)ethyl] methanesulfonamide hydrochloride | isomer 2 | 428 (M − HCl + 1) | K |
| 15 | N-[(1S)-2,2,2-trifluoro-1-(4-{[3-(pyridin-4-yl) piperidin-1-yl] methyl}phenyl)ethyl] methanesulfonamide hydrochloride | isomer 2 | 428 (M − HCl + 1) | H |
| 16 | N-[(1R)-1-(4-{[4-(1,3-benzothiazol-2-yl) piperidin-1-yl] methyl}phenyl)ethyl] methanesulfonamide hydrochloride | 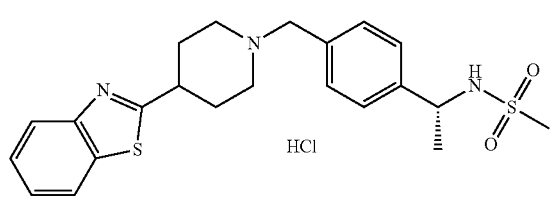 [SMILES: C[C@@H](NS(C)(=O)=O)c1ccc(CN2CCC(c3nc4ccccc4s3)CC2)cc1 ; Cl] | 430 (M − HCl + 1) | |

TABLE 6-continued

| Ex. # | Chemical name | Structure | Physical data MS (m/z): | Chrom Cond. |
|---|---|---|---|---|
| 17 | N-[(1R)-1-(4-{[4-(4-chlorophenyl)piperidin-1-yl]methyl}phenyl)ethyl]methanesulfonamide hydrochloride | 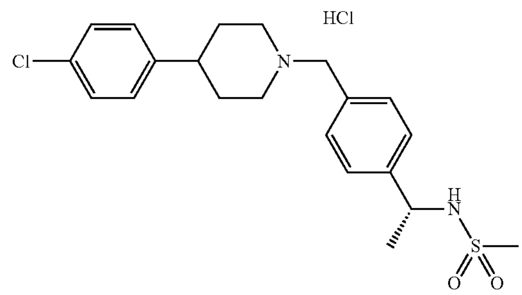 [SMILES: Cl ; C[C@@H](NS(C)(=O)=O)c1ccc(CN2CCC(c3ccc(Cl)cc3)CC2)cc1] | 407 (M − HCl + 1) | |
| 18 | N-[(1R)-1-(4-{[4-(1-methylethyl)piperidin-1-yl]methyl}phenyl)ethyl]methanesulfonamide hydrochloride | 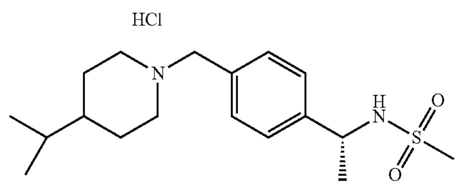 [SMILES: Cl ; CC(C)C1CCN(Cc2ccc([C@@H](C)NS(C)(=O)=O)cc2)CC1] | 339 (M − HCl + 1) | |
| 19 | N-[(1S)-1-(4-{[4-(1,3-benzothiazol-2-yl)piperidin-1-yl]methyl}phenyl)-2,2,2-trifluoroethyl]methanesulfonamide hydrochloride | 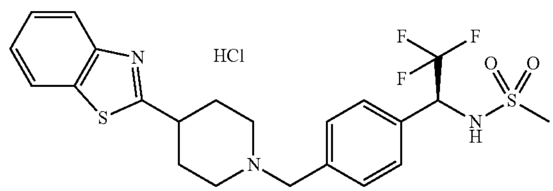 [SMILES: CS(=O)(=O)N[C@@H](c1ccc(CN2CCC(c3nc4ccccc4s3)CC2)cc1)C(F)(F)F ; Cl] | 484 (M − HCl + 1) | |
| 20 | N-[(1S)-2,2,2-trifluoro-1-(4-{[3-(1,3-thiazol-2-yl)piperidin-1-yl]methyl}phenyl)ethyl]methanesulfonamide hydrochloride | 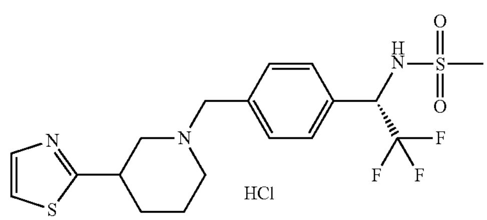 | 434 (M − HCl + 1) | C |
| 21 | N-{[(1R)-1-[4-({4-[4-(trifluoromethyl)phenyl]piperidin-1-yl}methyl)phenyl]ethyl}methanesulfonamide hydrochloride | 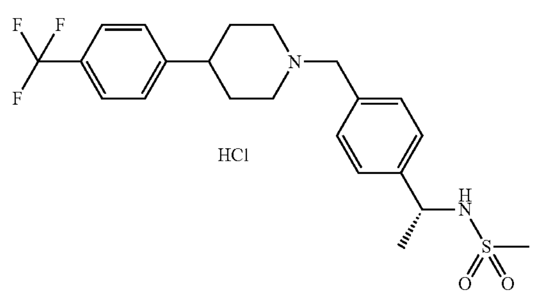 [SMILES: C[C@@H](NS(C)(=O)=O)c1ccc(CN2CCC(c3ccc(C(F)(F)F)cc3)CC2)cc1 ; Cl] | 441 (M − HCl + 1) | |
| 22 | N-[(1R)-1-(4-{[(3R,4R)-4-(4-fluorophenyl)-3-methoxypiperidin-1-yl]methyl}phenyl)ethyl]methanesulfonamide hydrochloride | 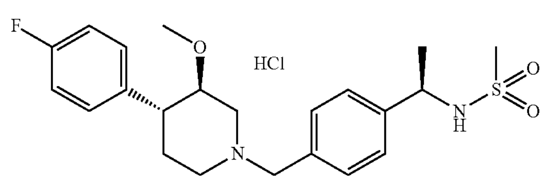 [SMILES: CO[C@H]1CN(Cc2ccc([C@@H](C)NS(C)(=O)=O)cc2)CC[C@@H]1c1ccc(F)cc1 ; Cl] | 421 (M − HCl + 1) | J |

TABLE 6-continued

| Ex. # | Chemical name | Structure | Physical data MS (m/z): | Chrom Cond. |
|---|---|---|---|---|
| 23 | N-[(1S)-1-{4-[(4-cyclobutylpiperidin-1-yl)methyl]phenyl}-2,2,2-trifluoroethyl]methanesulfonamide hydrochloride | 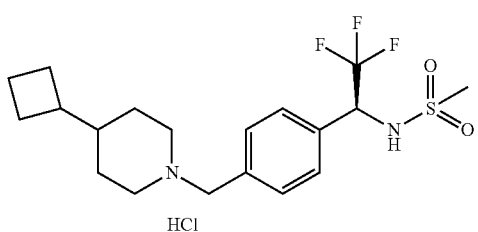 [SMILES: CS(=O)(=O)N[C@@H](c1ccc(CN2CCC(C3CCC3)CC2)cc1)C(F)(F)F ; Cl] | 405 (M − HCl + 1) | |
| 24 | N-[(1S)-2,2,2-trifluoro-1-(4-{[3-(4-fluorophenyl)piperidin-1-yl]methyl}phenyl)ethyl]methanesulfonamide hydrochloride | 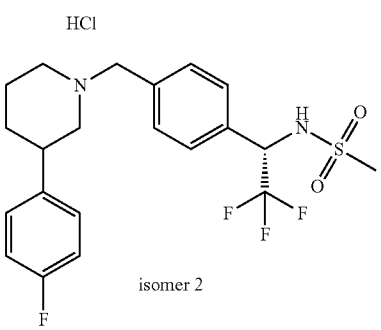 [SMILES: Cl ; CS(=O)(=O)N[C@@H](c1ccc(CN2CCCC(c3ccc(F)cc3)C2)cc1)C(F)(F)F] isomer 2 | 445 (M − HCl + 1) | D |
| 25 | N-[(1S)-2,2,2-trifluoro-1-(4-{[4-(6-methoxypyridin-2-yl)piperidin-1-yl]methyl}phenyl)ethyl]methanesulfonamide hydrochloride | 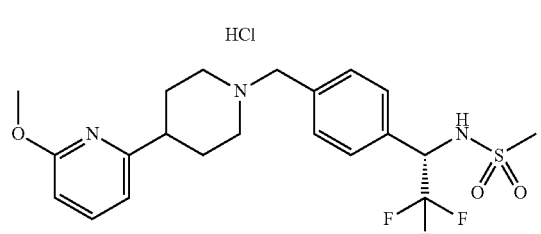 | 458 (M − HCl + 1) | |
| 26 | N-[(1S)-1-{4-[(3-tert-butylpiperidin-1-yl)methyl]phenyl}-2,2,2-trifluoroethyl]methanesulfonamide hydrochloride | 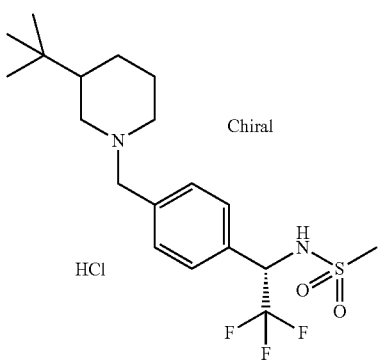 isomer 1 | 407 (M − HCl + 1) | R |

TABLE 6-continued

| Ex. # | Chemical name | Structure | Physical data MS (m/z): | Chrom Cond. |
|---|---|---|---|---|
| 27 | N-[(1R)-1-(4-{[(3S)-3-phenylpiperidin-1-yl]methyl}phenyl)ethyl]methanesulfonamide hydrochloride | 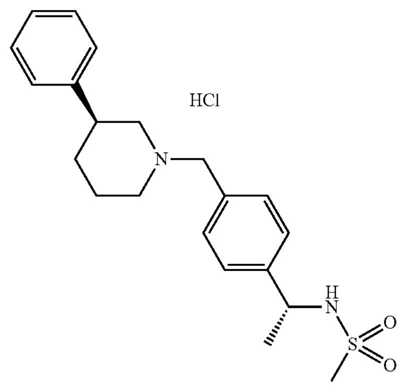 [SMILES: C[C@@H](NS(C)(=O)=O)c1ccc(CN2CCC[C@@H](c3ccccc3)C2)cc1 ; Cl] | 373 (M − HCl + 1) | |
| 28 | N-[(1S)-1-(4-{[4-(2-ethoxy-4-fluorophenyl)piperidin-1-yl]methyl}phenyl)-2,2,2-trifluoroethyl]methanesulfonamide hydrochloride | 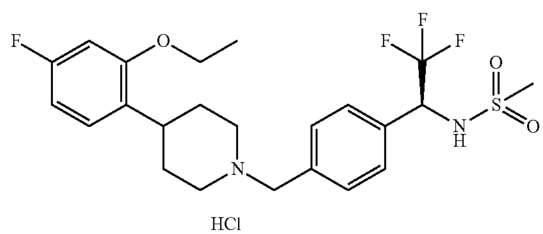 [SMILES: CCOc1cc(F)ccc1C1CCN(Cc2ccc([C@H](NS(C)(=O)=O)C(F)(F)F)cc2)CC1 ; Cl] | 489 (M − HCl + 1) | |
| 29 | N-[(1S)-1-(4-{[4-(6-ethoxypyridin-2-yl)piperidin-1-yl]methyl}phenyl)-2,2,2-trifluoroethyl]methanesulfonamide dihydrochloride | 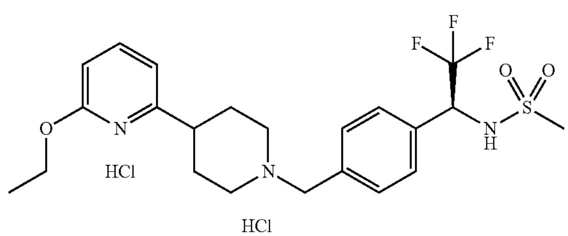 [SMILES: CCOc1cccc(C2CCN(Cc3ccc([C@H](NS(C)(=O)=O)C(F)(F)F)cc3)CC2)n1 ; Cl ; Cl] | 472 (M − HCl + 1) | |
| 30 | N-[(1S)-2,2,2-trifluoro-1-(4-{[4-methoxy-3-(1,3-thiazol-2-yl)piperidin-1-yl]methyl}phenyl)ethyl]methanesulfonamide hydrochloride | 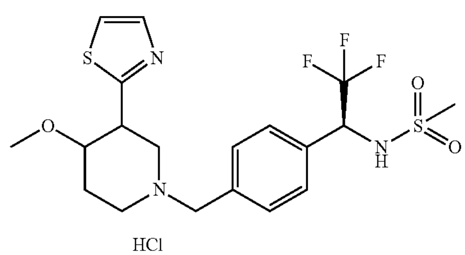 | 464 (M − HCl + 1) | M |
| 31 | N-{(1S)-2,2,2-trifluoro-1-[4-({4-[6-(1-methylethoxy)pyridin-2-yl]piperidin-1-yl}methyl)phenyl]ethyl}methanesulfonamide dihydrochloride | 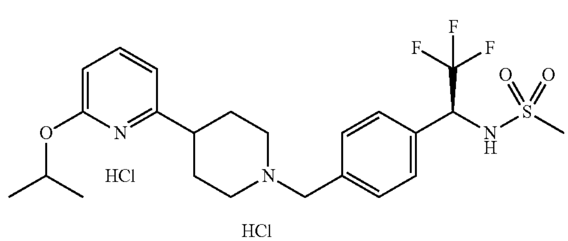 [SMILES: CC(C)Oc1cccc(C2CCN(Cc3ccc([C@H](NS(C)(=O)=O)C(F)(F)F)cc3)CC2)n1 ; Cl ; Cl] | 486 (M − HCl + 1) | |

TABLE 6-continued

| Ex. # | Chemical name | Structure | Physical data MS (m/z): | Chrom Cond. |
|---|---|---|---|---|
| 32 | N-[(1R)-1-(4-{[-3-ethoxy-4-(4-fluorophenyl)piperidin-1-yl]methyl}phenyl)ethyl]methanesulfonamide hydrochloride | 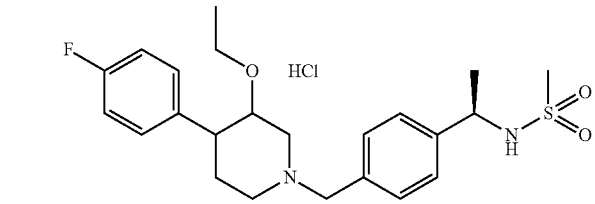 [SMILES: CCOC1CN(Cc2ccc([C@@H](C)NS(C)(=O)=O)cc2)CCC1c1ccc(F)cc1 ; Cl] | 435 (M − HCl + 1) | E |
| 33 | N-[(1S)-1-(4-{[4-(1-cyclopropylethyl)piperidin-1-yl]methyl}phenyl)-2,2,2-trifluoroethyl]methanesulfonamide hydrochloride isomer 1 | 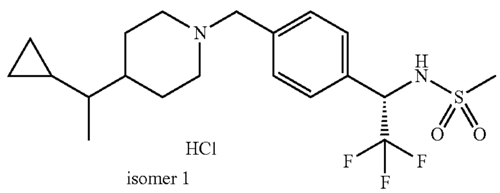 [SMILES: CC(C1CC1)C1CCN(Cc2ccc([C@H](NS(C)(=O)=O)C(F)(F)F)cc2)CC1 ; Cl] | 419 (M − HCl + 1) | |
| 34 | Trans-4-[(1S)-1-(4-{[3-ethoxy-4-(6-fluoropyridin-3-yl)piperidin-1-yl]methyl}phenyl)-2,2,2-trifluoroethyl]methanesulfonamide dihydrochloride isomer 1 | 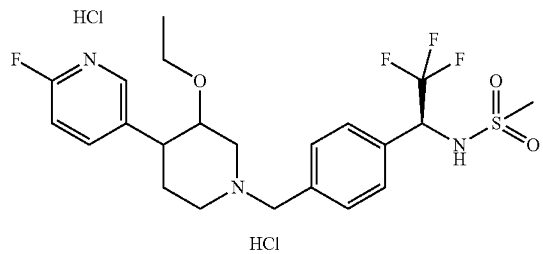 | 490 (M − HCl + 1) | Q[1] |
| 35 | N-{(1R)-1-[4-({4-[6-(cyclopropylmethoxy)pyridin-2-yl]piperidin-1-yl}methyl)phenyl]ethyl}methanesulfonamide hydrochloride | 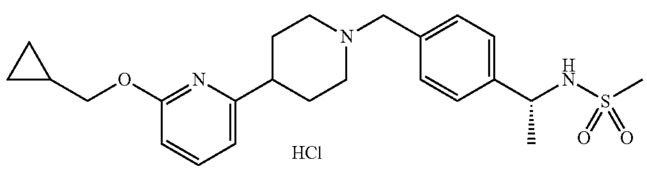 [SMILES: C[C@@H](NS(C)(=O)=O)c1ccc(CN2CCC(c3cccc(OCC4CC4)n3)CC2)cc1 ; Cl] | 444 (M − HCl + 1) | |
| 36 | N-{(1R)-1-[4-({4-[6-(1-methylethoxy)pyridin-2-yl]piperidin-1-yl}methyl)phenyl]ethyl}methanesulfonamide hydrochloride | 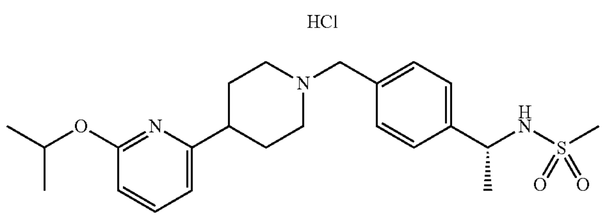 [SMILES: Cl ; CC(C)Oc1cccc(C2CCN(Cc3ccc([C@@H](C)NS(C)(=O)=O)cc3)CC2)n1] | 432 (M − HCl + 1) | |
| 37 | N-[(1S)-2,2,2-trifluoro-1-(4-{[4-(2-methoxy-6-methylpyridin-3-yl)piperidin-3-yl]methyl}phenyl)ethyl]methanesulfonamide | 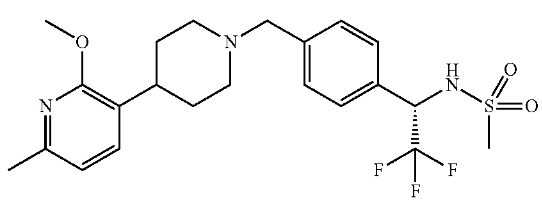 [SMILES: COc1nc(C)ccc1C1CCN(Cc2ccc([C@H](NS(C)(=O)=O)C(F)(F)F)cc2)CC1] | 472 (M + 1). | |
| 38 | N-[(1R)-1-(4-{[4-(6-ethoxypyridin-2-yl)piperidin-1-yl]methyl}phenyl)ethyl]methanesulfonamide hydrochloride | 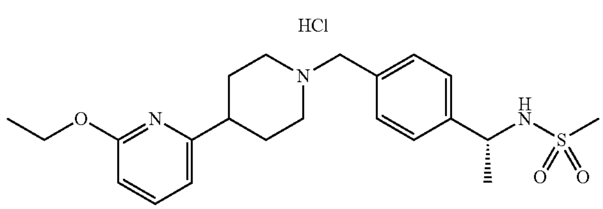 [SMILES: Cl ; CCOc1cccc(C2CCN(Cc3ccc([C@@H](C)NS(C)(=O)=O)cc3)CC2)n1] | 418 (M − HCl + 1) | |

TABLE 6-continued

| Ex. # | Chemical name | Structure | Physical data MS (m/z): | Chrom Cond. |
|---|---|---|---|---|
| 39 | N-{(1S)-1-[4-({4-[6-(cyclopropylmethoxy) pyridin-2-yl] piperidin-1-yl} methyl)phenyl]-2,2,2-trifluoroethyl} methanesulfonamide hydrochloride | 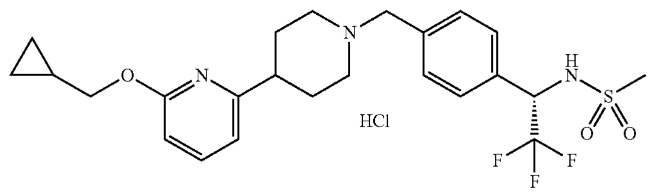 [SMILES: CS(=O)(=O)N[C@@H](c1ccc(CN2CCC(c3cccc(OCC4CC4)n3)CC2)cc1)C(F)(F)F ; Cl] | 498 (M − HCl + 1) | |
| 40 | Trans-N-[(1R)-1-(4-{[3-(difluoromethoxy)-4-(4-fluorophenyl) piperidin-1-yl] methyl}phenyl)ethyl] methanesulfonamide hydrochloride isomer 1 | 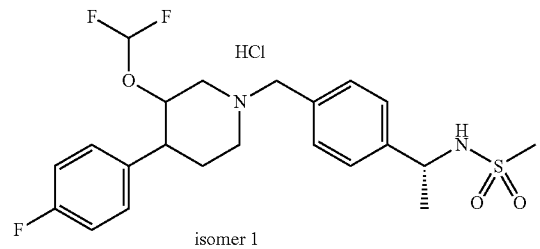 [SMILES: C[C@@H](NS(C)(=O)=O)c1ccc(CN2CCC(c3ccc(F)cc3)C(OC(F)F)C2)cc1 ; Cl] | 377 (M − HCl + 1) | N[1] |
| 41 | N-[(1R)-1-(4-{[4-(6-methoxypyridin-2-yl) piperidin-1-yl] methyl}phenyl)ethyl] methanesulfonamide hydrochloride | 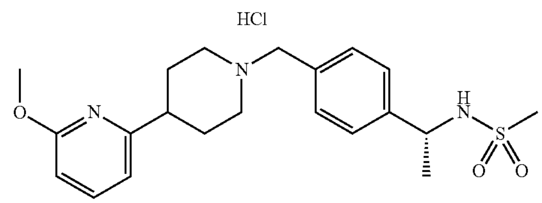 [SMILES: Cl ; COc1cccc(C2CCN(Cc3ccc([C@@H](C)NS(C)(=O)=O)cc3)CC2)n1] | 404 (M − HCl + 1) | O |
| 42 | N-[(1S)-1-(4-{[4-(1-cyclopropylethyl) piperidin-1-yl] methyl}phenyl)-2,2,2-trifluoroethyl] methanesulfonamide hydrochloride isomer 2 | 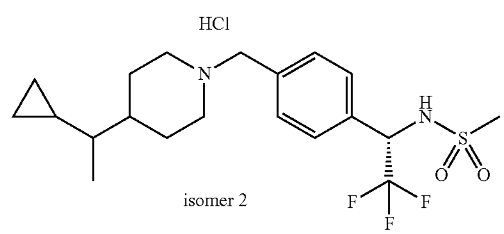 [SMILES: Cl ; CC(C1CC1)C1CCN(Cc2ccc([C@H](NS(C)(=O)=O)C(F)(F)F)cc2)CC1] | 491 (M − HCl + 1) | |
| 43 | N-[(1R)-1-(4-{[4-(1-cyclopropylethyl) piperidin-1-yl] methyl}phenyl)ethyl] methanesulfonamide hydrochloride isomer 2 | 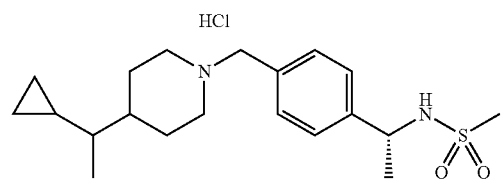 | 365 (M − HCl + 1) | |
| 44 | N-[(1R)-1-(4-{[4-(3,4-difluorophenyl) piperidin-1-yl] methyl}phenyl)ethyl] methanesulfonamide hydrochloride | 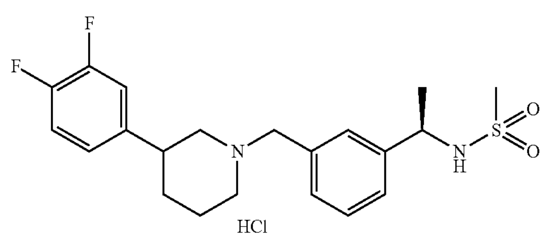 [SMILES: C[C@@H](NS(C)(=O)=O)c1cccc(CN2CCCC(c3ccc(F)c(F)c3)C2)c1 ; Cl] | 409 (M − HCl + 1) | |
| 45 | N-[(1R)-1-(4-{[4-(4-ethylphenyl) piperidin-1-yl] methyl}phenyl)ethyl] methanesulfonamide hydrochloride | 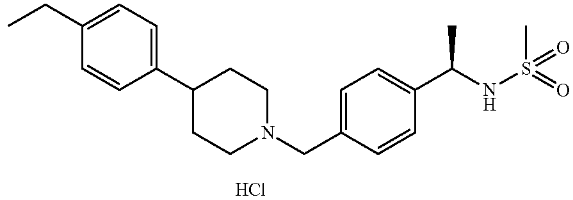 [SMILES: CCc1ccc(C2CCN(Cc3ccc([C@@H](C)NS(C)(=O)=O)cc3)CC2)cc1 ; Cl] | 401 (M − HCl + 1) | |

TABLE 6-continued

| Ex. # | Chemical name | Structure | Physical data MS (m/z): | Chrom Cond. |
|---|---|---|---|---|
| 46 | N-{[(1R)-1-[4-({4-[4-(trifluoromethoxy)phenyl]piperidin-1-yl}methyl)phenyl]ethyl}methanesulfonamide hydrochloride | 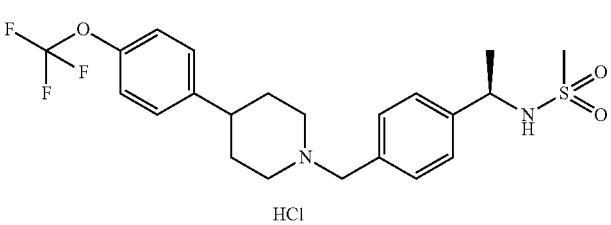 [SMILES: C[C@@H](NS(C)(=O)=O)c1ccc(CN2CCC(c3ccc(OC(F)(F)F)cc3)CC2)cc1 ; Cl] HCl | 457 (M − HCl + 1) | |
| 47 | N-[(1R)-1-(4-{[4-(3-chloro-4-fluorophenyl)piperidin-1-yl]methyl}phenyl)ethyl]methanesulfonamide hydrochloride | 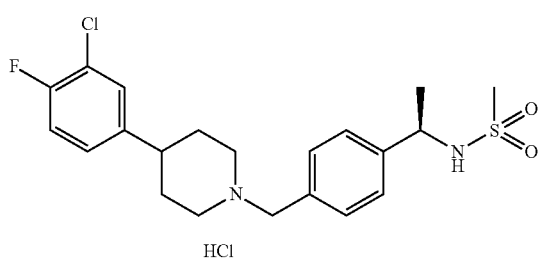 [SMILES: C[C@@H](NS(C)(=O)=O)c1ccc(CN2CCC(c3ccc(F)c(Cl)c3)CC2)cc1 ; Cl] HCl | 425 (M − HCl + 1) | |
| 48 | N-{(1R)-1-[4-({4-[4-(1-methylethoxy)phenyl]piperidin-1-yl}methyl)phenyl]ethyl}methanesulfonamide hydrochloride | 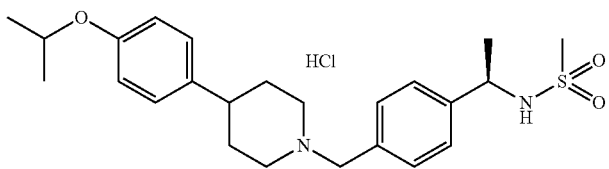 [SMILES: CC(C)Oc1ccc(C2CCN(Cc3ccc([C@@H](C)NS(C)(=O)=O)cc3)CC2)cc1 ; Cl] HCl | 401 (M − HCl + 1) | |
| 49 | N-[(1R)-1-(4-{[4-(2,4-difluorophenyl)piperidin-1-yl]methyl}phenyl)ethyl]methanesulfonamide | 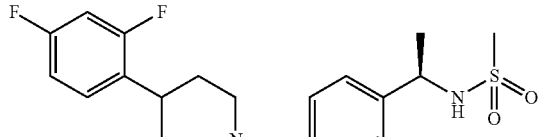 | 409 (M + 1) | |
| 50 | N-[(1R)-1-(4-{[4-(1-methylpropyl)piperidin-1-yl]methyl}phenyl)ethyl]methanesulfonamide hydrochloride | 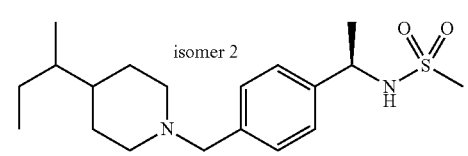 isomer 2 HCl | 353 (M − HCl + 1) | J |
| 51 | N-{(1R)-1-[4-({4-[3-(trifluoromethyl)phenyl]piperidin-1-yl}methyl)phenyl]ethyl}methanesulfonamide hydrochloride | 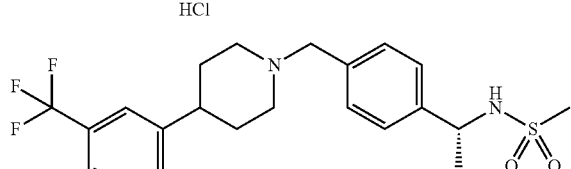 HCl | 441 (M − HCl + 1) | |

[1]The HCl salt was submitted for chromatographic separation

Chromatography conditions are noted where they vary from the Examples above.

TABLE 7

| Conditions | Column | Column Size | Mobile Phase |
|---|---|---|---|
| A | Chiralpak AD | 4.5 × 250 mm 10 um | Hexane/Isopropyl Alcohol 85/15 |
| B | Chiralcel OJ | 80 × 300 mm 20 um | Hexane/0.2% DMEA in EtOH 90/10 |

TABLE 7-continued

| Conditions | Column | Column Size | Mobile Phase |
|---|---|---|---|
| C | Chiralcel OJ | 20 × 250 mm 10 uM | Hexane/EtOH 75/25 |
| D | Chiralpak AD | 21.2 × 250 mm 5 um | Hexane/Isopropyl Alcohol 9/1 |
| E | Chiralpak AD-H | 21.2 × 250 mm 5 um | $CO_2$/EtOH-DMEA (0.2%) 75/25 |
| F | Chiralpak AD-H | 20 × 250 mm 5 um | $CO_2$/EtOH-DMEA (0.2%) 70/30 |
| G | Chiralpak AD-H | 20 × 250 mm 10 um | Hexane/0.2% DMEA in EtOH 95/5 |
| H | Chiralcel OJ | 20 × 250 mm 10 um | Hexane/EtOH 75/25 |
| I | Chiralcel OJ | 20 × 250 mm 10 um | Hexane/0.2% DMEA in EtOH 80/20 |
| J | Chiralpak AD-H | 21.2 × 250 mm 5 um | $CO_2$/EtOH-DMEA (0.2%) 80/20 |
| K | RP-C18 | 19 × 250 mm 15 um | 10 mM $NH_4HCO_3$/ACN 50-55% ACN gradient |
| L | Chiralpak AD-H | 21.2 × 250 mm 5 um | $CO_2$/EtOH-DMEA (0.2%) 85/15 |
| M | Chiralpak IC | 20 × 150 mm 5 um | $CO_2$/EtOH-DMEA (0.2%) 80/20 |
| N | Chiralpak AD-H | 21.2 × 250 mm 5 um | $CO_2$/MeOH-IPA (0.2%) 85/15 |
| O | Gimini C18 | 21 × 2 × 100 mm 6 um | ACN/$NH_4CO_3$—$H_2O$(10 mmol) 45-100% ACN gradient |
| P | Chiralpak AD-H | 21 × 250 mm 5 um | 10% MeOH/$CO_2$ |
| Q | Chiralpak AD-H | 20 × 250 mm 10 um | Hexane/0.2% DMEA in IPA 95/5 |
| R | IC-3 | 4.6 × 250 mm 5 um | gradient 25-100% of MeOH (0.1% DEA)/$CO_2$ |

MGAT-2 Inhibitory Assay

The in vitro inhibitory activity of compounds against human MGAT-2 is evaluated in this assay. MGAT-2 transfers an oleoyl group to monooleoyl-glycerol ("MAG") from oleoyl-CoA to form dioleoyl-glycerol ("DAG") in the intestinal triglyceride resynthesis pathway. The assay takes advantage of Microscint E extraction, which extracts hydrophobic molecules selectively over hydrophilic ones to separate the $^{14}$C-oleoyl-CoA from $^{14}$C-DAG.

Insect SF9 cells express human MGAT-2. Prepare the cell lysate in 20 mM of NaCl with protease inhibitor (Roche Cat#11873580001). Homogenize the SF9 cells expressing human MGAT-2 at 15,000 rpm for 20×2 seconds (PT-3100 Polytrone). Centrifuge the homogenate at 1000 g for 10 minutes at 4° C. Collect the supernatant into a separate tube for protein quantification and activity testing. Purify the glycerol monooleate substrate (Spectrum Chemical, CAS#25496-72-4) chromatographically. Prepare the monoacylglycerol (MAG) substrate in phospholipid vesicles (dioleoyl phosphatidylcholine "DOPC"). Prepare the MAG/DOPC vesicles at 20 mM concentration of total lipids (MAG and DOPC). Prepare different molar ratios of MAG to total lipids for either compound screening (8.9%) or compound kinetic studies (2.6-40%). Mix the appropriate amount of purified MAG and DOPC (Avanti Polar Lipids #850375C) in a glass tube under $N_2$ gas and then dry under vacuum for 30 minutes. Add an appropriate amount of buffer (Tris-Cl pH 7.4, 250 mM Sucrose, 1 mM EDTA) to the dried MAG/DOPC mixture for the desired MAG concentration. Sonicate the MAG/DOPC solution until the solution is clear. Measure the vesicle size under dynamic light scatter to confirm uniformity.

The assay buffer consists of 100 mM Tris, pH 7.5 (Invitrogen 15567-022), 11% DMSO, 250 mM Sucrose (Sigma S-0389), 1 mM, EDTA, and Complete Protease Inhibitor cocktail (Roche Diagnostic 12454800). Add compounds to the buffer together with the substrates and enzymes. The final concentration for the reaction is 0.016 mg/mL SF9 cell extract, 20 mM oleoyl-CoA (3.5 μM $^{14}$C-oleoyl-CoA), 1.26 mM of 8.9% MAG/DOPC vesicle. Stop the reaction after 90 minutes and incubation at room temperature by adding AESSM (12.5% 100% denatured EtOH; 11% DI H2O; 2.5% 1.0N NaOH; 59% Isopropanol (Mallinckrodt 3031-08); 15% Heptane (Omni Solv HX0078)). Add Microscint E and then seal the plates and count on a scintillation counter after at least 4 hours of equilibration at room temperature. Calculate the $IC_{50}$ (concentration to reach half maximum inhibition) using Excel Fit software (version 4; Data analyzing using a 4-parameter nonlinear logistic equation (ABase Equation 205)) by plotting concentration vs relative MGAT-2 activity.

The Examples disclosed herein exhibit an $IC_{50}$ of less than 80 nM in this MGAT-2 in vitro assay; and Example 1 exhibits an $IC_{50}$ of less than 12 nM. The results from this assay establish that the exemplified compounds inhibit the MGAT-2 enzyme in vitro.

Inhibitory Activity in MGAT-2 Cell Assay

The inhibitory activity of compounds against human MGAT-2 in a cell environment is evaluated in this assay. Caco-2 is a human colon carcinoma cell line and is often used as a model for intestinal epithelial cells. Caco-2 does not express MGAT-2, and, thus, human MGAT-2 is engineered into the cell line through a stable transfection. A MAG analogue, 2-O-Hexadecylglycerol (HDG), is utilized to detect cellular MGAT-2 activity, because HDG is not be hydrolyzed and the resulting product is readily monitored by mass spectrometry. The substrate is delivered to cells using phospholipid vesicles.

Seed the Caco2 cells onto 100 mm dishes to be 80% confluent after 24 hours in complete media (3/1 DMEM: F12+10% FBS+20 mM HEPES+gentamicin). Transfect the cells with hMGAT-2 plasmid (MGAT-2-pCDNA3.1-Hygro) using Lipofectamine 2000 (Invitrogen). After a 6 hour exposure to the transfection mixture, wash the cells 3× in PBS and then add media. Incubate the cells for an additional 18 hours incubation, trypsinize the cells and serially dilute them into 100 mm dishes. Added complete media+400 μg/ml hygromycin and incubate until clones appear. Isolate and transfer the clones into 24 well dishes and grow to confluency. Prepare the RNAs from these clones using a Qiagen RNAeasy kit. Perform Taqman analysis using an ABI inventoried assay (HS00228262) on a 7900 Sequence Detection System (ABI). Analyze the lysates from these clones western blot analysis using a goat polyclonal antibody (Santa Cruz, SC-32392 to confirm human MGAT-2 expression of a 38 Kdal protein corresponding to MGAT-2.

Mix 2-O-hexadecylglycerol ("HDG", Biosynth Chemistry & Biology, # H-1806, 562.7 μl of 20 mg/ml) and DOPC (14.3 ml of 20 mg/ml) in a glass tube; dry first under $N_2$ gas; and then under vacuum for additional 30 minutes. Add 20 ml of buffer (150 mM Tris-Cl pH 7.4, 250 mM Sucrose, 1 mM EDTA) to the dried HDG/DOPC mixture while sonicating until the solution becomes clear. Plate the Caco2 cells into a poly-D-lysine coated 96-well plate (the "Cell Plate") at 37° C., 5% $CO_2$ overnight. Remove the growth media and pretreat the cells with the test compound in DMEMF12 (3:1) media (GIBCO 93-0152DK) containing 2% BSA (Sigma) for 30 minutes. Treat the cells with one test compound in 2% BSA DMEMF12 (3:1) media containing 40 μM of oleic acid and 800 μM of 8.9% HDG/DOPC for 4 hours. Trypsinize the cells with 50 μl of trypsin and add 50 μl of PBS. Immediately freeze the cells on dry ice and store at −20° C. for LC-MS analysis. Extract the cells with chloroform/methanol as follows transfer the cells to a 2 ml Plate; wash the Cell Plate with 200 μL methanol and then transfer the methanol wash to the 2 ml Plate; wash the Cell Plate again with 200 μL PBS and transfer the PBS wash to the 2 ml Plate. Add chloroform (400 μL) with internal standard (19.52 ng/mL) DAG (15:0,15:0 (Sigma)), D5-TAG (39.03 ng/mL) CDN (16,16,16) to the 2 mL Plate. Mix the 2 mL Plate up and down (10×), then vortex and spin. Remove 400 μL of the lower layer from the 2 mL plate and add to the wells of another plate the "Final Plate". Add $CHCl_3$:MeOH (400 μL 2:1) to the 2 mL Plate. Again mix the 2 mL Plate up and down (10×), vortex and spin. Remove 220 μL of the lower layer from the 2 mL Plate and add to the Final Plate. Dry the Final Plate and reconstitute with 500 mL of IPA. Seal the Final Plate and shake for 5 min. Inject 10 μl of a sample from the Final Plate onto a Halo C8 column (2.1×50, 2.7 uL particle size) held at 60° C. using a Leap auto sampler with a 10 μL loop, interfaced to a Shimadzu solvent delivery system. Monitor the channels to collect data for the D5 C16 TAG internal standard as well as the ether TAG, and C52 and C54 natural TAGs. Solvent A is 80/20 $H_2O$/Methanol with 20 μM ammonium acetate. Solvent B is 50/50 IPA/THF with 20 μM ammonium acetate. Flow rate is 0.4 mL/min. Wash solvents were $H_2O$/MeOH and DCM. Using Xcalibur extract the areas of the peaks of interest, and export the data to Excel which uses the following formula: (area of ether TAG/area of C54 natural TAG)/Area of IS. This ratio effectively accounts for variance of cell number in each well. The resulting data for Examples 1, 2, 4, and 5 are listed below in Table 8.

MGAT-2 Cell Assay

TABLE 8

| Example | Basal Triglyceride Caco 2 Relative $IC_{50}$ (μM) |
| --- | --- |
| Example 1 HCl salt | 0.0582 (n = 14) |
| Example 2 Phosphoric acid salt | 0.102 (n = 1) |
| Example 4 | 0.0177 (, n = 6) |
| Example 5 | 0.0642 (, n = 10) |

The results of the MGAT-2 cell based assay demonstrate that the Examples listed above in Table 8 inhibit the human MGAT-2 in the cell environment.

Pharmacological Effects in a Dog Oil Bolus Model

Inhibiting MGAT-2 found in the small intestine may be useful for treating hypertriglyceridemia caused by excessive fat intake. To assess the ability of the exemplified compounds to inhibit TAG absorption, twenty one male beagles (n=7 per treatment group) are enrolled for each study each dog selected to have a body weight between 9-13 kg. House the dogs in cages with a standard light cycle (12 hours light and 12 hours dark); at room temperature: 72±8° F.; and at 30%-70% relative humidity. Fast the dogs for 16 hours prior to the start of the study, then dose the fasted dogs with vehicle (1% HEC, 0.25%, Tween 80, Antifoam) or one of the test compounds. Bleed the dogs one hour after dosing, (0.5 ml from the jugular vein) for a time 0 sample. Dose the dogs with olive oil (Sigma Catalog#: O-1514, 5 ml/kg) immediately after collection of the time 0 sample. Collect samples into an EDTA tube on ice at 1.5, 2, 3, 5, 7, and 9 hrs post compound/vehicle dosing. Centrifuge the samples at 9000 cpm for 15 min and analyze (Roche Cat no. 1877771) for plasma total triglyceride using a Roche Hitachi 917. For plasma/Serum TAG18.1_18.1_18.1 measurement, extract the samples and perform LC/MS/MS analysis similarly to that described above in MGAT-2 Cell Assay using 10 μL of plasma/serum.

The analyte is the [M+NH4]+ ion of TAG 18:1 18:1 18:1, which has a mass of 902.8 m/z; the internal standard is D5 TAG 16:0 16:0 16:0, which has a mass of 829.8 m/z. Report the ratio of the 603.5 m/z daughter ion of 902.8 m/z (TAG 18:1 18:1 18:1) and the 556.5 m/z daughter ion of 829.8 m/z (D5 TAG 16:0 16:0 16:0 internal standard) changes in TAG 18:1 18:1 18:1 relative amount. Calculate the net plasma TAG AUC from total TAG AUC minus baseline TAG AUC using Graphpad Prism4: (Net $AUC_{TAG}$=$AUC_{TAG}$ post oil bolus–$AUC_{TAG}$ at 0 hour). The percent inhibition of plasma triglyceride is calculated as follows: the (oil bolus group mean of net TAG AUC–oil bolus group mean of net TAG AUC with compound treatment/oil bolus group mean of net TAG AUC) *100. The final statistic analysis uses Dunnett's method of One way Anova for comparison with the control. All Net TAG AUC values are transformed to ranked averaged AUC for comparison to limit the variability of the studies.

Example 1, when dosed at 10 mg/kg inhibited TAG absorption by 69%; and when Example 1 was dosed at 30 mg/kg it completely inhibited TAG absorption. These data demonstrate that Example 1 effectively inhibits MGAT-2 activity and reduces TAG absorption in vivo.

Exemplified compounds of the present invention can be readily formulated into pharmaceutical compositions in accordance within accepted practices such as found in Remington's Pharmaceutical Sciences, Gennaro, Ed., Mack Publishing Co. Easton Pa. 1990. Preferred pharmaceutical compositions can be formulated as a tablet or capsule for oral administration. The tablet or capsule can include a compound of the present invention in an effective amount for treating a patient in need of treatment.

What is claimed is:

1. A compound of the formula below:

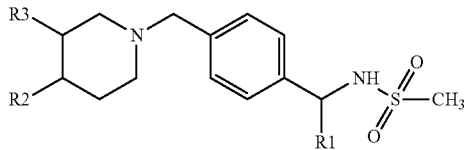

wherein

R1 is selected from: —CH₃ and —CF₃;

R2 is selected from H, —C₁₋₄alkyl, —C₃₋₄cycloalkyl, —C₁₋₂alkylcyclopropyl, —O—C₁₋₂alkyl, phenyl, 2-benzothiazolyl, 2-pyridinyl, and 3-pyridinyl, wherein the phenyl is optionally substituted with 1 or 2 groups independently selected from: halogen, —C₁₋₂alkyl, —CF₃, —OC₁₋₃alkyl, and —OC₁₋₂haloalkyl, and the pyridinyl is optionally substituted with 1 or 2 groups independently selected from —CH₃, halogen, —OCH₂cyclopropyl, and —OC₁₋₃alkyl; and R3 is selected from: H, —OC₁₋₄alkyl, —OC₁₋₃alkyl, —OC₁₋₂haloalkyl, phenyl, 2-pyridinyl, 3-pyridinyl, 4-pyridinyl, and 2-thiazolyl, wherein the phenyl is optionally substituted with a halogen; provided that if one of R2 and R3 is H then the other one of R2 and R3 is not H;

or a pharmaceutically acceptable salt thereof.

2. A compound according to claim 1, or a pharmaceutically acceptable salt thereof, wherein R1 is —CH₃.

3. A compound according to claim 1, or a pharmaceutically acceptable salt thereof, wherein R1 is —CF₃.

4. A compound according to claim 1, or a pharmaceutically acceptable salt thereof, wherein R2 is selected from —C₁₋₄alkyl, —C₃₋₄cycloalkyl, —O—CH₃, and phenyl, wherein the phenyl is optionally substituted with a halogen.

5. A compound according to claim 1, or a pharmaceutically acceptable salt thereof, wherein R2 is selected from —C(CH₃)₃, cyclopropyl, —O—CH₃, and phenyl, wherein the phenyl is optionally substituted with a halogen.

6. A compound according to claim 1, or a pharmaceutically acceptable salt thereof, wherein R2 is selected from: —C(CH₃)₃, —OCH₃, and 4-fluorophenyl.

7. A compound according to claim 1, or a pharmaceutically acceptable salt thereof, wherein R3 is selected from: H, phenyl, —OCH₃, 2-pyridinyl, 3-pyridinyl, and 2-thiazolyl, wherein the phenyl is optionally substituted with a halogen.

8. A compound according to claim 1, or a pharmaceutically acceptable salt thereof, wherein R3 is selected from: H, phenyl, and 2-thiazolyl, wherein the phenyl is optionally substituted with a halogen.

9. A compound according to claim 1, or a pharmaceutically acceptable salt thereof, wherein R3 is H.

10. A compound according to claim 1, or a pharmaceutically acceptable salt thereof, wherein
R1 is —CF₃;
R2 is —C(CH₃)₃ or —OCH₃; and
R3 is H or 2-thiazolyl.

11. A compound which is N-[(1S)-1-[4-[(4-tert-butyl-1-piperidyl)methyl]phenyl]-2,2,2-trifluoro-ethyl]methanesulfonamide, or a pharmaceutically acceptable salt thereof.

12. A compound of according to claim 1 wherein the pharmaceutically acceptable salt is a chloride salt or phosphate salt.

13. A compound of according to claim 11 wherein the pharmaceutically acceptable salt is a chloride salt or phosphate salt.

14. A pharmaceutical composition comprising a compound according to claim 1 or a pharmaceutically acceptable salt thereof and at least one of a pharmaceutically acceptable carrier, diluent, or excipient.

15. A method of treating a patient in need of treatment for hypertriglyceridemia, the method comprises administering to the patient an effective amount of a compound, or a pharmaceutically acceptable salt thereof, according to claim 1.

* * * * *